United States Patent
Hochman et al.

(10) Patent No.: US 9,452,032 B2
(45) Date of Patent: Sep. 27, 2016

(54) SOFT TISSUE PRESERVATION TEMPORARY (SHELL) IMMEDIATE-IMPLANT ABUTMENT WITH BIOLOGICAL ACTIVE SURFACE

(71) Applicant: Biomet 3i LLC, Palm Beach Gardens, FL (US)

(72) Inventors: Mark N. Hochman, Great Neck, NY (US); Stephen J. Chu, New York, NY (US); Jocelyn Huiping Tan-Chu, New York, NY (US); Adam J. Mieleszko, Arverne, NY (US)

(73) Assignee: BIOMET 3I, LLC, Palm Beach Gardens, FL (US)

( * ) Notice: Subject to any disclaimer, the term of this patent is extended or adjusted under 35 U.S.C. 154(b) by 0 days.

(21) Appl. No.: 13/928,460

(22) Filed: Jun. 27, 2013

(65) Prior Publication Data
US 2013/0288202 A1    Oct. 31, 2013

Related U.S. Application Data

(63) Continuation-in-part of application No. 13/655,056, filed on Oct. 18, 2012, now Pat. No. 9,089,382, which is a continuation-in-part of application No. 13/356,359, filed on Jan. 23, 2012, now Pat. No. 8,425,231.

(51) Int. Cl.
*A61C 8/00* (2006.01)
*A61C 8/02* (2006.01)
(Continued)

(52) U.S. Cl.
CPC ............. *A61C 8/008* (2013.01); *A61C 1/084* (2013.01); *A61C 8/0001* (2013.01);
(Continued)

(58) Field of Classification Search
USPC .............................. 433/172–176, 72–76, 136
See application file for complete search history.

(56) References Cited

U.S. PATENT DOCUMENTS

RE27,227 E    11/1971    Harnesberger
3,906,634 A    9/1975    Aspel
(Continued)

FOREIGN PATENT DOCUMENTS

DE    10029256    11/2000
EP    0 747 017    12/1996
(Continued)

OTHER PUBLICATIONS

Areva, S., et al., "Use of sol-gel-derived titania coating for direct soft tissue attachment", Jun. 2, 2004, Wiley Periodicals, Inc., Turku, Finland.
(Continued)

*Primary Examiner* — Yogesh Patel
(74) *Attorney, Agent, or Firm* — Schwegman Lundberg & Woessner, P.A.

(57) ABSTRACT

An immediate dental implant shell has outer, multiple zones for engaging a soft tissue socket left immediately after tooth extraction from a bone socket. The zones have combinations of different biologic agents, macro- or micro-geometric, or micro- or macro-morphology irregularities to better engage gingival sulcus, junctional epithelium and dento-gingival fiber zones of the soft tissue socket. The shell may also have various guide markings and projections to aide drilling of the implant hole in the bone socket. A dental implant is placed in the drilled implant hole before or after the shell has been placed in the soft tissue socket, and has an axis that is independent of the shell axis so the shell and implant both sit in optimum positions in their respective soft and bone sockets.

14 Claims, 9 Drawing Sheets

(51) Int. Cl.
*A61C 1/08* (2006.01)
*A61C 9/00* (2006.01)
*A61C 13/107* (2006.01)
*A61C 13/00* (2006.01)

(52) U.S. Cl.
CPC .......... *A61C 8/0006* (2013.01); *A61C 8/0077* (2013.01); *A61C 9/004* (2013.01); *A61C 13/0001* (2013.01); *A61C 13/0004* (2013.01); *A61C 2008/0046* (2013.01)

(56) References Cited

U.S. PATENT DOCUMENTS

| | | | |
|---|---|---|---|
| 3,919,772 A | 11/1975 | Lenczycki | |
| 3,958,471 A | 5/1976 | Muller | |
| 4,011,602 A | 3/1977 | Rybicki et al. | |
| 4,056,585 A | 11/1977 | Waltke | |
| 4,086,701 A | 5/1978 | Kawahara et al. | |
| 4,177,562 A | 12/1979 | Miller et al. | |
| 4,294,544 A | 10/1981 | Altschuler et al. | |
| 4,306,862 A | 12/1981 | Knox | |
| 4,325,373 A | 4/1982 | Slivenko et al. | |
| 4,341,312 A | 7/1982 | Scholer | |
| 4,364,381 A | 12/1982 | Sher et al. | |
| 4,439,152 A | 3/1984 | Small | |
| 4,543,953 A | 10/1985 | Slocum et al. | |
| 4,547,157 A | 10/1985 | Driskell | |
| 4,571,180 A | 2/1986 | Kulick | |
| 4,611,288 A | 9/1986 | Duret et al. | |
| 4,624,673 A | 11/1986 | Meyer | |
| 4,663,720 A | 5/1987 | Duret et al. | |
| 4,713,004 A | 12/1987 | Linkow et al. | |
| 4,756,689 A | 7/1988 | Lundgren | |
| 4,758,161 A | 7/1988 | Niznick | |
| 4,767,331 A | 8/1988 | Hoe | |
| 4,772,204 A | 9/1988 | Soderberg | |
| 4,821,200 A | 4/1989 | Öberg | |
| 4,842,518 A | 6/1989 | Linkow et al. | |
| 4,850,870 A | 7/1989 | Lazzara et al. | |
| 4,850,873 A | 7/1989 | Lazzara et al. | |
| 4,854,872 A | 8/1989 | Detsch | |
| 4,856,994 A | 8/1989 | Lazzara et al. | |
| 4,872,839 A | 10/1989 | Brajnovic | |
| 4,906,191 A | 3/1990 | Soderberg | |
| 4,906,420 A | 3/1990 | Brajnovic | |
| 4,931,016 A | 6/1990 | Sillard | |
| 4,935,635 A | 6/1990 | O'Harra | |
| 4,955,811 A | 9/1990 | Lazzara et al. | |
| 4,961,674 A | 10/1990 | Wang et al. | |
| 4,964,770 A | 10/1990 | Steinbichler et al. | |
| 4,986,753 A | 1/1991 | Sellers | |
| 4,988,297 A | 1/1991 | Lazzara et al. | |
| 4,988,298 A | 1/1991 | Lazzara et al. | |
| 4,998,881 A | 3/1991 | Lauks | |
| 5,000,685 A | 3/1991 | Brajnovic | |
| 5,006,069 A | 4/1991 | Lazzara et al. | |
| 5,015,183 A | 5/1991 | Fenick | |
| 5,015,186 A | 5/1991 | Detsch | |
| 5,030,096 A | 7/1991 | Hurson et al. | |
| 5,035,619 A | 7/1991 | Daftary | |
| 5,040,982 A | 8/1991 | Stefan-Dogar | |
| 5,040,983 A | 8/1991 | Binon | |
| 5,064,375 A | 11/1991 | Jörnéus | |
| 5,071,351 A | 12/1991 | Green, Jr. et al. | |
| 5,073,111 A | 12/1991 | Daftary | |
| 5,087,200 A | 2/1992 | Brajnovic et al. | |
| 5,100,323 A | 3/1992 | Friedman et al. | |
| 5,104,318 A | 4/1992 | Piche et al. | |
| 5,106,300 A | 4/1992 | Voitik | |
| 5,122,059 A | 6/1992 | Dürr et al. | |
| 5,125,839 A | 6/1992 | Ingber et al. | |
| 5,125,841 A | 6/1992 | Carlsson et al. | |
| 5,133,660 A | 7/1992 | Fenick | |
| 5,135,395 A | 8/1992 | Marlin | |
| 5,145,371 A | 9/1992 | Jörnéus | |
| 5,145,372 A | 9/1992 | Daftary et al. | |
| 5,176,516 A | 1/1993 | Koizumi | |
| 5,188,800 A | 2/1993 | Green, Jr. et al. | |
| 5,195,892 A | 3/1993 | Gersberg | |
| 5,205,745 A | 4/1993 | Kamiya et al. | |
| 5,209,659 A | 5/1993 | Friedman et al. | |
| 5,209,666 A | 5/1993 | Balfour et al. | |
| 5,213,502 A | 5/1993 | Daftary | |
| 5,221,204 A | 6/1993 | Kruger et al. | |
| 5,237,998 A | 8/1993 | Duret et al. | |
| 5,246,370 A | 9/1993 | Coatoam | |
| 5,257,184 A | 10/1993 | Mushabac | |
| 5,281,140 A | 1/1994 | Niznick | |
| 5,286,195 A | 2/1994 | Clostermann | |
| 5,286,196 A | 2/1994 | Brajnovic et al. | |
| 5,292,252 A | 3/1994 | Nickerson et al. | |
| 5,297,963 A | 3/1994 | Dafatry | |
| 5,302,125 A | 4/1994 | Kownacki et al. | |
| 5,312,254 A | 5/1994 | Rosenlicht | |
| 5,312,409 A | 5/1994 | McLaughlin et al. | |
| 5,316,476 A | 5/1994 | Krauser | |
| 5,320,529 A | 6/1994 | Pompa | |
| 5,328,371 A | 7/1994 | Hund et al. | |
| 5,334,024 A | 8/1994 | Niznick | |
| 5,336,090 A | 8/1994 | Wilson, Jr. et al. | |
| 5,338,196 A | 8/1994 | Beaty et al. | |
| 5,338,198 A | 8/1994 | Wu et al. | |
| 5,343,391 A | 8/1994 | Mushabac | |
| 5,344,457 A | 9/1994 | Pilliar et al. | |
| 5,350,297 A | 9/1994 | Cohen | |
| 5,359,511 A | 10/1994 | Schroeder et al. | |
| 5,362,234 A | 11/1994 | Salazar et al. | |
| 5,362,235 A | 11/1994 | Daftary | |
| 5,368,483 A | 11/1994 | Sutter et al. | |
| 5,370,692 A | 12/1994 | Fink | |
| 5,372,502 A | 12/1994 | Massen et al. | |
| 5,386,292 A | 1/1995 | Massen et al. | |
| 5,413,481 A | 5/1995 | Göppel et al. | |
| 5,417,568 A | 5/1995 | Diglio | |
| 5,417,569 A | 5/1995 | Perisse | |
| 5,417,570 A | 5/1995 | Zuest et al. | |
| 5,419,702 A | 5/1995 | Beaty et al. | |
| 5,431,567 A | 7/1995 | Datary | |
| 5,433,606 A | 7/1995 | Niznick et al. | |
| 5,437,551 A | 8/1995 | Chalifoux | |
| 5,440,393 A | 8/1995 | Wenz | |
| 5,452,219 A | 9/1995 | Dehoff et al. | |
| 5,458,488 A | 10/1995 | Chalifoux | |
| 5,476,382 A | 12/1995 | Daftary | |
| 5,476,383 A | 12/1995 | Beaty et al. | |
| 5,492,471 A | 2/1996 | Singer | |
| 5,516,288 A | 5/1996 | Sichler et al. | |
| 5,527,182 A | 6/1996 | Willoughby | |
| 5,533,898 A | 7/1996 | Mena | |
| 5,538,426 A | 7/1996 | Harding et al. | |
| 5,547,377 A | 8/1996 | Daftary | |
| 5,556,278 A | 9/1996 | Meitner | |
| 5,564,921 A | 10/1996 | Marlin | |
| 5,564,924 A | 10/1996 | Kwan | |
| 5,569,578 A | 10/1996 | Mushabac | |
| 5,571,016 A | 11/1996 | Ingber et al. | |
| 5,575,656 A | 11/1996 | Hajjar | |
| 5,580,244 A | 12/1996 | White | |
| 5,580,246 A | 12/1996 | Fried | |
| 5,595,703 A | 1/1997 | Swaelens et al. | |
| 5,599,185 A | 2/1997 | Greenberg | |
| 5,613,832 A | 3/1997 | Su | |
| 5,613,852 A | 3/1997 | Bavitz | |
| 5,630,717 A | 5/1997 | Zuest | |
| 5,636,986 A | 6/1997 | Prezeshkian | |
| 5,651,675 A | 7/1997 | Singer | |
| 5,652,709 A | 7/1997 | Andersson et al. | |
| 5,658,147 A | 8/1997 | Phimmasone | |
| 5,662,476 A | 9/1997 | Ingber et al. | |
| 5,674,069 A * | 10/1997 | Osorio | 433/172 |
| 5,674,071 A | 10/1997 | Beaty et al. | |
| 5,674,073 A | 10/1997 | Ingber et al. | |
| 5,681,167 A | 10/1997 | Lazarof | |
| 5,685,714 A | 11/1997 | Beaty et al. | |

(56) References Cited

U.S. PATENT DOCUMENTS

| | | | |
|---|---|---|---|
| 5,685,715 A | 11/1997 | Beaty et al. |
| 5,688,283 A | 11/1997 | Knapp |
| 5,704,936 A | 1/1998 | Mazel |
| 5,718,579 A | 2/1998 | Kennedy |
| 5,725,376 A | 3/1998 | Poirier |
| 5,733,124 A | 3/1998 | Kwan |
| 5,741,215 A | 4/1998 | D'Urso |
| 5,743,916 A | 4/1998 | Greenberg |
| 5,759,036 A | 6/1998 | Hinds |
| 5,762,125 A | 6/1998 | Mastrorio |
| 5,762,500 A | 6/1998 | Lazarof |
| 5,768,134 A | 6/1998 | Swaelens et al. |
| 5,769,636 A | 6/1998 | Di Sario |
| 5,779,481 A | 7/1998 | Aires |
| 5,791,902 A | 8/1998 | Lauks |
| 5,800,168 A | 9/1998 | Cascione et al. |
| 5,810,589 A | 9/1998 | Michnick et al. |
| 5,810,592 A | 9/1998 | Daftary |
| 5,813,858 A | 9/1998 | Singer |
| 5,823,778 A | 10/1998 | Schmitt et al. |
| 5,842,859 A | 12/1998 | Palacci |
| 5,846,079 A | 12/1998 | Knode |
| 5,851,115 A | 12/1998 | Carlsson et al. |
| 5,857,853 A | 1/1999 | Van Nifterick et al. |
| 5,871,358 A | 2/1999 | Ingber et al. |
| 5,873,722 A | 2/1999 | Lazzara et al. |
| 5,876,204 A | 3/1999 | Day et al. |
| 5,885,078 A | 3/1999 | Cagna et al. |
| 5,888,034 A | 3/1999 | Greenberg |
| 5,890,902 A | 4/1999 | Sapian |
| 5,899,695 A | 5/1999 | Lazzara et al. |
| 5,899,697 A | 5/1999 | Lazzara et al. |
| 5,904,483 A | 5/1999 | Wade |
| 5,915,962 A | 6/1999 | Rosenlicht |
| 5,927,982 A | 7/1999 | Kruger |
| 5,931,675 A | 8/1999 | Callan |
| 5,938,443 A | 8/1999 | Lazzara et al. |
| 5,947,732 A | 9/1999 | Beaty et al. |
| 5,954,769 A | 9/1999 | Rosenlicht |
| 5,964,591 A | 10/1999 | Beaty et al. |
| 5,967,777 A | 10/1999 | Klein et al. |
| 5,984,681 A | 11/1999 | Huang |
| 5,989,025 A | 11/1999 | Conley |
| 5,989,026 A | 11/1999 | Rogers et al. |
| 5,989,029 A | 11/1999 | Osorlo |
| 5,989,258 A | 11/1999 | Hattori |
| 5,997,681 A | 12/1999 | Kinzie |
| 6,000,939 A | 12/1999 | Ray et al. |
| 6,008,905 A | 12/1999 | Breton et al. |
| 6,030,219 A | 2/2000 | Zuest et al. |
| 6,068,479 A | 5/2000 | Kwan |
| 6,099,311 A | 8/2000 | Wagner et al. |
| 6,099,313 A | 8/2000 | Dorken et al. |
| 6,099,314 A | 8/2000 | Kopelman et al. |
| 6,120,293 A | 9/2000 | Lazzara et al. |
| 6,129,548 A | 10/2000 | Lazzara et al. |
| 6,135,773 A | 10/2000 | Lazzara |
| 6,142,782 A | 11/2000 | Lazarof |
| 6,152,737 A | 11/2000 | Beaty et al. |
| 6,164,969 A * | 12/2000 | Dinkelacker ............... 433/173 |
| 6,168,435 B1 | 1/2001 | Beaty et al. |
| 6,174,168 B1 | 1/2001 | Dehoff et al. |
| 6,175,413 B1 | 1/2001 | Lucas |
| 6,190,169 B1 | 2/2001 | Bluemli et al. |
| 6,197,410 B1 | 3/2001 | Vallittu et al. |
| 6,200,125 B1 | 3/2001 | Akutagawa |
| 6,206,693 B1 | 3/2001 | Hultgren |
| 6,210,162 B1 | 4/2001 | Chishti |
| 6,217,334 B1 | 4/2001 | Hultgren |
| 6,227,857 B1 | 5/2001 | Morgan |
| 6,227,859 B1 | 5/2001 | Sutter |
| 6,283,753 B1 | 9/2001 | Willoughby |
| 6,287,117 B1 | 9/2001 | Niznick |
| 6,287,119 B1 | 9/2001 | van Nifterick |
| 6,296,483 B1 | 10/2001 | Champleboux |
| 6,305,939 B1 | 10/2001 | Dawood |
| 6,312,259 B1 | 11/2001 | Kvarnstrom et al. |
| 6,319,000 B1 | 11/2001 | Branemark |
| 6,322,728 B1 | 11/2001 | Brodkin |
| 6,343,930 B1 | 2/2002 | Beaty et al. |
| 6,382,975 B1 | 5/2002 | Poirier |
| 6,402,707 B1 | 6/2002 | Ernst |
| 6,419,491 B1 | 7/2002 | Ricci et al. |
| 6,426,114 B1 | 7/2002 | Troczynski et al. |
| 6,428,803 B1 | 8/2002 | Ewers et al. |
| 6,431,866 B1 | 8/2002 | Hurson |
| 6,431,867 B1 | 8/2002 | Gittelson et al. |
| 6,482,444 B1 | 11/2002 | Bellantone et al. |
| 6,488,503 B1 | 12/2002 | Lichkus et al. |
| 6,497,573 B2 | 12/2002 | Wagner et al. |
| 6,497,574 B1 | 12/2002 | Miller |
| 6,537,069 B1 | 3/2003 | Simmons, Jr. |
| 6,540,784 B2 | 4/2003 | Barlow |
| 6,558,162 B1 | 5/2003 | Porter et al. |
| 6,568,936 B2 | 5/2003 | MacDougald |
| 6,575,751 B1 | 6/2003 | Lehmann et al. |
| 6,594,539 B1 | 7/2003 | Geng |
| 6,610,079 B1 | 8/2003 | Li |
| 6,619,958 B2 | 9/2003 | Beaty et al. |
| 6,629,840 B2 | 10/2003 | Chishti |
| 6,634,883 B2 | 10/2003 | Ranalli |
| 6,644,970 B1 | 11/2003 | Lin |
| 6,648,640 B2 | 11/2003 | Rubbert et al. |
| 6,663,388 B1 | 12/2003 | Schär et al. |
| 6,671,539 B2 | 12/2003 | Gateno et al. |
| 6,672,870 B2 | 1/2004 | Knapp |
| 6,688,887 B2 | 2/2004 | Morgan |
| 6,691,764 B2 | 2/2004 | Embert |
| 6,743,491 B2 | 6/2004 | Cirincione et al. |
| 6,755,652 B2 | 6/2004 | Nanni |
| 6,772,026 B2 | 8/2004 | Bradbury |
| 6,776,614 B2 | 8/2004 | Wiechmann et al. |
| 6,783,359 B2 | 8/2004 | Kapit |
| 6,790,040 B2 | 9/2004 | Amber et al. |
| 6,793,491 B2 | 9/2004 | Klein et al. |
| 6,808,659 B2 | 10/2004 | Schulman |
| 6,814,575 B2 | 11/2004 | Poirier |
| 6,821,462 B2 | 11/2004 | Schulamn et al. |
| 6,829,498 B2 | 12/2004 | Kipke et al. |
| D503,804 S | 4/2005 | Phleps et al. |
| 6,882,894 B2 | 4/2005 | Durbin et al. |
| 6,885,464 B1 | 4/2005 | Pfeiffer et al. |
| 6,902,401 B2 | 6/2005 | Jorneus et al. |
| 6,913,463 B2 | 7/2005 | Blacklock |
| 6,926,442 B2 | 8/2005 | Stöckl |
| 6,926,525 B1 | 8/2005 | Ronvig |
| 6,939,489 B2 | 9/2005 | Moszner et al. |
| 6,942,699 B2 | 9/2005 | Stone et al. |
| 6,953,383 B2 | 10/2005 | Rothenberger |
| 6,957,118 B2 | 10/2005 | Kopelman et al. |
| 6,966,772 B2 | 11/2005 | Malin et al. |
| 6,970,760 B2 | 11/2005 | Wolf et al. |
| 6,971,877 B2 | 12/2005 | Harter |
| 6,984,392 B2 | 1/2006 | Bechert et al. |
| 6,994,549 B2 | 2/2006 | Brodkin et al. |
| 7,010,150 B1 | 3/2006 | Pfeiffer et al. |
| 7,010,153 B2 | 3/2006 | Zimmermann |
| 7,012,988 B2 | 3/2006 | Adler et al. |
| 7,018,207 B2 | 3/2006 | Prestipino |
| 7,021,934 B2 | 4/2006 | Aravena |
| 7,029,275 B2 | 4/2006 | Rubbert et al. |
| 7,044,735 B2 | 5/2006 | Malin |
| 7,056,115 B2 | 6/2006 | Phan et al. |
| 7,056,117 B2 | 6/2006 | Simmons, Jr. |
| 7,056,472 B1 | 6/2006 | Behringer |
| 7,059,856 B2 | 6/2006 | Marotta |
| 7,066,736 B2 | 6/2006 | Kumar et al. |
| 7,067,169 B2 | 6/2006 | Liu et al. |
| 7,084,868 B2 | 8/2006 | Farag et al. |
| 7,086,860 B2 | 8/2006 | Schuman et al. |
| 7,097,451 B2 | 8/2006 | Tang |
| 7,104,795 B2 | 9/2006 | Dadi |
| 7,110,844 B2 | 9/2006 | Kopelman |
| 7,112,065 B2 | 9/2006 | Kopelman |

(56) References Cited

U.S. PATENT DOCUMENTS

| | | |
|---|---|---|
| 7,118,375 B2 | 10/2006 | Durbin et al. |
| D532,991 S | 12/2006 | Gozzi |
| 7,153,132 B2 | 12/2006 | Tedesco |
| 7,153,135 B1 | 12/2006 | Thomas |
| 7,163,443 B2 | 1/2007 | Basler et al. |
| 7,175,434 B2 | 2/2007 | Brajnovic |
| 7,175,435 B2 | 2/2007 | Andersson et al. |
| 7,178,731 B2 | 2/2007 | Basler |
| 7,214,062 B2 | 5/2007 | Morgan |
| 7,220,124 B2 | 5/2007 | Taub et al. |
| 7,228,191 B2 | 6/2007 | Hofmeister et al. |
| 7,236,842 B2 | 6/2007 | Kopelman et al. |
| 7,281,927 B2 | 10/2007 | Marotta |
| 7,286,954 B2 | 10/2007 | Kopelman et al. |
| 7,303,420 B2 | 12/2007 | Huch et al. |
| 7,319,529 B2 | 1/2008 | Babayoff |
| 7,322,746 B2 | 1/2008 | Beckhaus et al. |
| 7,322,824 B2 | 1/2008 | Schmitt |
| 7,324,680 B2 | 1/2008 | Zimmermann |
| 7,329,122 B1 | 2/2008 | Scott |
| 7,333,874 B2 | 2/2008 | Taub et al. |
| 7,335,876 B2 | 2/2008 | Eiff et al. |
| D565,184 S | 3/2008 | Royzen |
| 7,338,286 B2 | 3/2008 | Porter et al. |
| 7,341,756 B2 | 3/2008 | Liu et al. |
| 7,367,801 B2 | 5/2008 | Saliger |
| 7,379,584 B2 | 5/2008 | Rubbert et al. |
| D571,471 S | 6/2008 | Stöckl |
| 7,381,191 B2 | 6/2008 | Fallah |
| 7,383,094 B2 | 6/2008 | Kopelman et al. |
| D575,747 S | 8/2008 | Abramovich et al. |
| 7,421,608 B2 | 9/2008 | Schron |
| 7,425,131 B2 | 9/2008 | Amber et al. |
| 7,429,175 B2 | 9/2008 | Gittelson |
| 7,435,088 B2 | 10/2008 | Brajnovic |
| 7,476,100 B2 | 1/2009 | Kuo |
| 7,481,647 B2 | 1/2009 | Sambu et al. |
| 7,484,959 B2 | 2/2009 | Porter et al. |
| 7,488,174 B2 | 2/2009 | Kopelman et al. |
| 7,491,058 B2 | 2/2009 | Jorneus et al. |
| 7,497,619 B2 | 3/2009 | Stoeckl |
| 7,497,983 B2 | 3/2009 | Khan et al. |
| 7,520,747 B2 | 4/2009 | Stonisch |
| 7,522,764 B2 | 4/2009 | Schwotzer |
| 7,534,266 B2 | 5/2009 | Kluger |
| 7,536,234 B2 | 5/2009 | Kopelman et al. |
| 7,545,372 B2 | 6/2009 | Kopelman et al. |
| 7,551,760 B2 | 6/2009 | Scharlack et al. |
| 7,555,403 B2 | 6/2009 | Kopelman et al. |
| 7,556,496 B2 | 7/2009 | Cinader, Jr. et al. |
| 7,559,692 B2 | 7/2009 | Beckhaus et al. |
| 7,563,397 B2 | 7/2009 | Schulman et al. |
| D597,769 S | 8/2009 | Richter et al. |
| 7,572,058 B2 | 8/2009 | Pruss et al. |
| 7,572,125 B2 | 8/2009 | Brajnovic |
| 7,574,025 B2 | 8/2009 | Feldman |
| 7,578,673 B2 | 8/2009 | Wen et al. |
| 7,580,502 B2 | 8/2009 | Dalpiaz et al. |
| 7,581,951 B2 | 9/2009 | Lehmann et al. |
| 7,582,855 B2 | 9/2009 | Pfeiffer |
| 7,628,537 B2 | 12/2009 | Schulze-Ganzlin |
| 7,632,097 B2 | 12/2009 | Clerck |
| 7,653,455 B2 | 1/2010 | Cnader, Jr. et al. |
| 7,654,823 B2 | 2/2010 | Dadi |
| 7,655,586 B1 | 2/2010 | Brodkin et al. |
| 7,658,610 B2 | 2/2010 | Knopp |
| 7,661,956 B2 | 2/2010 | Powell et al. |
| 7,665,989 B2 | 2/2010 | Brajnovic et al. |
| 7,679,723 B2 | 3/2010 | Schwotzer |
| 7,687,754 B2 | 3/2010 | Eiff et al. |
| 7,689,308 B2 | 3/2010 | Holzner et al. |
| D614,210 S | 4/2010 | Basler et al. |
| 7,698,014 B2 | 4/2010 | Dunne et al. |
| 7,758,346 B1 | 7/2010 | Letcher |
| 7,774,084 B2 | 8/2010 | Cinader, Jr. |
| 7,780,446 B2 | 8/2010 | Sanchez et al. |
| 7,780,907 B2 | 8/2010 | Schmidt et al. |
| 7,785,007 B2 | 8/2010 | Stoeckl |
| 7,787,132 B2 | 8/2010 | Körner et al. |
| 7,796,811 B2 | 9/2010 | Orth et al. |
| 7,798,708 B2 | 9/2010 | Erhardt et al. |
| 7,801,632 B2 | 9/2010 | Orth et al. |
| 7,815,371 B2 | 10/2010 | Schulze-Ganzlin |
| 7,824,181 B2 | 11/2010 | Sers |
| D629,908 S | 12/2010 | Jerger et al. |
| 7,855,354 B2 | 12/2010 | Eiff |
| 7,865,261 B2 | 1/2011 | Pfeiffer |
| 7,876,877 B2 | 1/2011 | Stockl |
| 7,901,209 B2 | 3/2011 | Saliger et al. |
| 7,906,132 B2 | 3/2011 | Ziegler et al. |
| 7,982,731 B2 | 7/2011 | Orth et al. |
| 7,985,119 B2 | 7/2011 | Basler et al. |
| 7,986,415 B2 | 7/2011 | Thiel et al. |
| 7,988,449 B2 | 8/2011 | Amber et al. |
| 8,011,925 B2 | 9/2011 | Powell et al. |
| 8,011,927 B2 | 9/2011 | Merckmans, III et al. |
| 8,026,943 B2 | 9/2011 | Weber et al. |
| 8,033,826 B2 | 10/2011 | Towse et al. |
| 8,038,440 B2 | 10/2011 | Swaelens et al. |
| 8,043,091 B2 | 10/2011 | Schmitt |
| 8,047,895 B2 | 11/2011 | Basler |
| 8,057,912 B2 | 11/2011 | Basler et al. |
| 8,062,034 B2 | 11/2011 | Hanisch et al. |
| 8,075,313 B2 | 12/2011 | Ranck et al. |
| 8,083,522 B2 | 12/2011 | Karkar et al. |
| 8,105,081 B2 | 1/2012 | Bavar |
| 8,185,224 B2 | 5/2012 | Powell et al. |
| 8,226,654 B2 | 7/2012 | Ranck et al. |
| 8,257,083 B2 | 9/2012 | Berckmans, III et al. |
| 8,272,870 B2 | 9/2012 | Van Lierde |
| 8,309,162 B2 | 11/2012 | Charlton et al. |
| 8,602,783 B2 | 12/2013 | Fudim |
| 2001/0008751 A1 | 7/2001 | Chishti et al. |
| 2001/0034010 A1 | 10/2001 | MacDougald et al. |
| 2002/0010568 A1 | 1/2002 | Rubbert et al. |
| 2002/0028418 A1 | 3/2002 | Farag et al. |
| 2002/0039717 A1* | 4/2002 | Amber et al. ............ 433/172 |
| 2002/0160337 A1 | 10/2002 | Klein et al. |
| 2002/0167100 A1 | 11/2002 | Moszner |
| 2003/0130605 A1 | 7/2003 | Besek |
| 2003/0222366 A1 | 12/2003 | Stangel |
| 2004/0029074 A1 | 2/2004 | Brajnovic |
| 2004/0048227 A1 | 3/2004 | Brajnovic |
| 2004/0121286 A1 | 6/2004 | Aravena et al. |
| 2004/0132603 A1 | 7/2004 | Narhi et al. |
| 2004/0180308 A1 | 9/2004 | Ebi et al. |
| 2004/0219477 A1 | 11/2004 | Harter |
| 2004/0219479 A1 | 11/2004 | Malin et al. |
| 2004/0219490 A1 | 11/2004 | Gartner et al. |
| 2004/0220691 A1 | 11/2004 | Hofmeister et al. |
| 2004/0241611 A1 | 12/2004 | Amber et al. |
| 2004/0243481 A1 | 12/2004 | Bradbury et al. |
| 2004/0259051 A1 | 12/2004 | Brajnovic |
| 2005/0023710 A1 | 2/2005 | Brodkin et al. |
| 2005/0056350 A1 | 3/2005 | Dolabdjian et al. |
| 2005/0070782 A1 | 3/2005 | Brodkin |
| 2005/0084144 A1 | 4/2005 | Feldman |
| 2005/0100861 A1 | 5/2005 | Choi et al. |
| 2005/0170311 A1 | 8/2005 | Tardieu et al. |
| 2005/0271996 A1 | 12/2005 | Sporbert et al. |
| 2005/0277089 A1 | 12/2005 | Brajnovic |
| 2005/0277090 A1 | 12/2005 | Anderson et al. |
| 2005/0277091 A1 | 12/2005 | Andersson et al. |
| 2005/0282106 A1 | 12/2005 | Sussman et al. |
| 2005/0283065 A1 | 12/2005 | Babayoff |
| 2006/0006561 A1 | 1/2006 | Brajnovic |
| 2006/0008763 A1 | 1/2006 | Brajnovic |
| 2006/0008770 A1 | 1/2006 | Brajnovic et al. |
| 2006/0046229 A1 | 3/2006 | Teich |
| 2006/0064758 A1 | 3/2006 | Petner et al. |
| 2006/0093988 A1 | 5/2006 | Swaelens et al. |
| 2006/0094951 A1 | 5/2006 | Dean et al. |
| 2006/0127848 A1 | 6/2006 | Sogo et al. |
| 2006/0210949 A1 | 9/2006 | Stoop |

(56) References Cited

U.S. PATENT DOCUMENTS

| | | |
|---|---|---|
| 2006/0240385 A1 | 10/2006 | Gatti |
| 2006/0252009 A1 | 11/2006 | Gogarnoiu |
| 2006/0263741 A1 | 11/2006 | Imgrund et al. |
| 2006/0281041 A1 | 12/2006 | Rubbert et al. |
| 2007/0015111 A1 | 1/2007 | Kopelman et al. |
| 2007/0031790 A1 | 2/2007 | Raby et al. |
| 2007/0065777 A1 | 3/2007 | Becker |
| 2007/0077532 A1 | 4/2007 | Harter |
| 2007/0092854 A1 | 4/2007 | Powell et al. |
| 2007/0141525 A1 | 6/2007 | Cinader, Jr. |
| 2007/0211081 A1 | 9/2007 | Quadling et al. |
| 2007/0218426 A1 | 9/2007 | Quadling et al. |
| 2007/0264612 A1 | 11/2007 | Mount |
| 2007/0269769 A1 | 11/2007 | Marchesi |
| 2007/0281277 A1 | 12/2007 | Brajnovic |
| 2008/0038692 A1 | 2/2008 | Andersson et al. |
| 2008/0044794 A1 | 2/2008 | Brajnovic |
| 2008/0057467 A1 | 3/2008 | Gittelson |
| 2008/0070181 A1 | 3/2008 | Abolfathi et al. |
| 2008/0085489 A1 | 4/2008 | Schmitt |
| 2008/0090210 A1 | 4/2008 | Brajnovic |
| 2008/0114371 A1 | 5/2008 | Kluger |
| 2008/0118895 A1 | 5/2008 | Brajnovic |
| 2008/0124676 A1 | 5/2008 | Marotta |
| 2008/0153060 A1 | 6/2008 | De Moyer |
| 2008/0153061 A1 | 6/2008 | Marcello |
| 2008/0153065 A1 | 6/2008 | Brajnovic et al. |
| 2008/0153069 A1 | 6/2008 | Holzner et al. |
| 2008/0176189 A1 | 7/2008 | Stonisch |
| 2008/0206714 A1 | 8/2008 | Schmitt |
| 2008/0233537 A1 | 9/2008 | Amber et al. |
| 2008/0233539 A1 | 9/2008 | Rossler et al. |
| 2008/0241798 A1 | 10/2008 | Holzner et al. |
| 2008/0261165 A1 | 10/2008 | Steingart et al. |
| 2008/0261176 A1 | 10/2008 | Hurson |
| 2008/0286722 A1 | 11/2008 | Berckmans, III et al. |
| 2008/0300716 A1 | 12/2008 | Kopelman et al. |
| 2009/0017418 A1 | 1/2009 | Gittelson |
| 2009/0026643 A1 | 1/2009 | Wiest et al. |
| 2009/0042167 A1 | 2/2009 | Van Der Zel |
| 2009/0081616 A1 | 3/2009 | Pfeiffer |
| 2009/0087817 A1 | 4/2009 | Jansen et al. |
| 2009/0092948 A1 | 4/2009 | Gantes |
| 2009/0098510 A1 | 4/2009 | Zhang |
| 2009/0098511 A1 | 4/2009 | Zhang |
| 2009/0123045 A1 | 5/2009 | Quadling et al. |
| 2009/0123887 A1 | 5/2009 | Brajnovic |
| 2009/0130630 A1 | 5/2009 | Suttin et al. |
| 2009/0186319 A1 | 7/2009 | Sager |
| 2009/0187393 A1 | 7/2009 | Van Lierde et al. |
| 2009/0220134 A1 | 9/2009 | Cahill et al. |
| 2009/0220916 A1 | 9/2009 | Fisker et al. |
| 2009/0220917 A1 | 9/2009 | Jensen |
| 2009/0239195 A1 | 9/2009 | Wohrle et al. |
| 2009/0239197 A1* | 9/2009 | Brajnovic ............... 433/174 |
| 2009/0239200 A1 | 9/2009 | Brajnovic et al. |
| 2009/0253097 A1 | 10/2009 | Brajnovic |
| 2009/0263764 A1 | 10/2009 | Berckmans, III et al. |
| 2009/0287332 A1 | 11/2009 | Adusumilli et al. |
| 2009/0298009 A1 | 12/2009 | Brajnovic |
| 2009/0298017 A1 | 12/2009 | Boerjes et al. |
| 2009/0317763 A1 | 12/2009 | Brajnovic |
| 2009/0325122 A1 | 12/2009 | Brajnovic et al. |
| 2010/0009314 A1 | 1/2010 | Tardieu et al. |
| 2010/0028827 A1 | 2/2010 | Andersson et al. |
| 2010/0038807 A1 | 2/2010 | Brodkin et al. |
| 2010/0075275 A1 | 3/2010 | Brajnovic |
| 2010/0092904 A1 | 4/2010 | Esposti et al. |
| 2010/0105008 A1 | 4/2010 | Powell et al. |
| 2010/0151420 A1 | 6/2010 | Ranck |
| 2010/0151423 A1 | 6/2010 | Ranck et al. |
| 2010/0173260 A1 | 7/2010 | Sogo et al. |
| 2010/0209877 A1 | 8/2010 | Hogan et al. |
| 2010/0280798 A1 | 11/2010 | Pattijn et al. |
| 2010/0330533 A1 | 12/2010 | Cottrell |
| 2011/0008751 A1 | 1/2011 | Pettersson |
| 2011/0027339 A1 | 2/2011 | Mao |
| 2011/0060558 A1 | 3/2011 | Pettersson |
| 2011/0123959 A1 | 5/2011 | Sicurelli |
| 2011/0129792 A1 | 6/2011 | Berckmans, III et al. |
| 2011/0159455 A1 | 6/2011 | Stumpel |
| 2011/0183289 A1 | 7/2011 | Powell et al. |
| 2011/0191081 A1 | 8/2011 | Malfliet et al. |
| 2011/0200967 A1 | 8/2011 | Laizure, Jr. |
| 2011/0244426 A1 | 10/2011 | Amber et al. |
| 2011/0269104 A1 | 11/2011 | Berckmans, III et al. |
| 2011/0275032 A1 | 11/2011 | Tardieu et al. |
| 2011/0306008 A1 | 12/2011 | Suttin et al. |
| 2011/0306009 A1 | 12/2011 | Suttin et al. |
| 2011/0306014 A1 | 12/2011 | Conte et al. |
| 2012/0010740 A1 | 1/2012 | Swaelens et al. |
| 2012/0135370 A1 | 5/2012 | Ranck et al. |
| 2012/0164593 A1 | 6/2012 | Bavar |
| 2012/0164893 A1 | 6/2012 | Mitsuzuka et al. |
| 2012/0214130 A1 | 8/2012 | Krivoruk |
| 2012/0282573 A1 | 11/2012 | Mao |
| 2012/0330315 A1 | 12/2012 | Ranck et al. |
| 2013/0101964 A1* | 4/2013 | Fudim ............... 433/214 |
| 2015/0289952 A1 | 10/2015 | Hochman et al. |

FOREIGN PATENT DOCUMENTS

| | | |
|---|---|---|
| JP | 2008531095 A | 8/2008 |
| WO | WO 94/26200 | 11/1994 |
| WO | WO 99/32045 | 7/1999 |
| WO | WO 00/08415 | 2/2000 |
| WO | WO 01/58379 | 8/2001 |
| WO | WO 02/053055 | 7/2002 |
| WO | WO 03/024352 | 3/2003 |
| WO | WO2004037110 A1 * | 10/2003 |
| WO | WO 2004/030565 | 4/2004 |
| WO | WO 2004/075771 | 9/2004 |
| WO | WO 2004/087000 | 10/2004 |
| WO | WO 2004/098435 | 11/2004 |
| WO | WO 2006/014130 | 2/2006 |
| WO | WO 2006/062459 | 6/2006 |
| WO | WO 2006/082198 | 8/2006 |
| WO | WO 2007/005490 | 1/2007 |
| WO | WO 2007/033157 | 3/2007 |
| WO | WO 2007/104842 | 9/2007 |
| WO | WO 2007/129955 | 11/2007 |
| WO | WO 2008/057955 | 5/2008 |
| WO | WO 2008/083857 | 7/2008 |
| WO | WO 2009/146164 | 12/2009 |

OTHER PUBLICATIONS

Rossi, S., et al., "Peri-implant tissue response to TiO2 surface modified implants", 2008, Blackwell Manksgaard, Turku, Finland.

BIOMET 3i—Manual entitled "Navigator™ System for CT Guided Surgery Manual", Revision A Oct. 2007—34 pages.

Francois Goulette, "A New Method and a Clinical case for Computer Assisted Dental Implantology." Retrieved from Summer European university in surgical Robotics, URL:www.lirmm.fr/manifs/UEE/docs/students/goulette.pdf, Sep. 6, 2003 (7 pages).

Jakob Brief, "Accuracy of image-guided implantology." Retrieved from Google, <URL:sitemaker.umich.edu/sarmentlab/files/robodent_vs_denx_coir_05.pdf, Aug. 20, 2004, (7 pages).

Machine Design: "Robots are ready for medical manufacturing." Retrieved from MachineDesign.Com, <URL: http://machinedesign.com/article/robots-are-ready-for-medical-manufacturing-0712>, Jul. 12, 2007 (7 pages).

MedNEWS: "'Surgical Glue' May Help to Eliminate Suturing for Implants." Retrieved from MediNEWS.Direct, URL:http://www.medinewsdirect.com/?p=377, Dec. 21, 2007 (1 page).

U.S. Appl. No. 14/749,377, Preliminary Amendment filed Jun. 24, 2015, 7 pgs.

U.S. Appl. No. 14/749,377, Preliminary Amendment filed Jun. 25, 2015, 7 pgs.

European Application Serial No. 12866657.5, Extended European Search Report mailed Sep. 14, 2015, 8 pgs.

(56) References Cited

OTHER PUBLICATIONS

International Application Serial No. PCT/US2012/68078, International Search Report mailed Feb. 15, 2013, 3 pgs.

International Application Serial No. PCT/US2012/68078, Written Opinion mailed Feb. 15, 2013, 5 pgs.

Japanese Application Serial No. 2014-553294, Office Action mailed Mar. 16, 2016, (With English Translation), 7 pgs.

Frojd, Victoria, et al., "Effect of Nanoporous TiO2 Coating and Anodized Ca2 Modification of Titanium Surfaces on Early Microbial Biofilm Formation", BMC Oral Health, (2011), 9 pgs.

Nevins, Myron, et al., "Histologic Evidence of a Connective Tissue Attachment to Laser Microgrooved Abutments: A Canine Study", The Int'l Jml of Perio. & Rest. Dentistry, vol. 30, No. 3, (2010), 12 pgs.

Rossi, Sarni, et al., "Peri-implant tissue response to TiO2 surface modified implants", Clin. Oral Impl. Res.19, (2009), 348-355 pgs.

"Immediate Provisional Restoration of Implants with PreFormance Provisional Components", Biomet 3i et al., PreFormance Temporary Cylinder Brochure, (2007), 6 pgs.

"NanoTite Prevail Implants: Crestal Bone Preservation in Aesthetic Zone", Biomet 3i, ARTIOI IA NanoTite Implant System Brochure, vol. 6, Issue 2, (2007), 1 pg.

"Osseotite Implants, Restorative Manual", Biomet 3i, (2009), 116 pgs.

"Provisionalization with Soft Tissue Sculpting Prior to Fabrication of a CAD/CAM Abutment", Biomet 3i et al., ART1060 EncodeCP Brochure, vol. 7, Issue 3, (2009), 8 pgs.

"Rapid Adjustment. Enduring Strength Aesthetic Design", Biomet 3i, ART953C PreFormance Brochure, (2008), 4 pgs.

"Restoration of Immediate Temporary Crown Cases: Guidance", OsseoNews, [Online] retrieved from the internet: <http://www.osseonews.com/restoration-of-immediate-temporary-crown-cases-guidance/>, (Mar. 20, 2009), 6 pgs.

"Your Patients Require Immediate Aesthetic Solutions . . . Biomet 3i Has Optimal Products", Biomet 3i, ARTI 018 Provisional Components Brochure, (2009), 5 pgs.

Giordano, Russell, "Zirconia: A Proven, Durable Ceramic for Esthetic Restorations", Compendium, Clinical Materials Review, vol. 33, No. 1, (2012), 4 pgs.

Joseph, Y K, et al., "Immediate Placement and Provisionalization of Maxillary Anterior Single Implants: A Surgical and Prosth. Rationale", Pract. Periodont Aesthet.Dent., (2000), 817-824 pgs.

Joseph, Y K, et al., "Interimplant Papilla Preservation in the Esthetic Zone: A Report of Six Consecutive Cases", The Int'l Jml of Perio. & Rest. Dentistry, vol. 23, No. 3, (2003), 12 pgs.

Perry, Ronald D, et al., "Provisional Materials: Key Components of Interim Fixed Restorations", (2012), 3 pgs.

Wohrle, Peter S, "Single-Tooth Replacement in the Aesthetic Zone with Immediate Provisionalization: Fourteen Consecutive Case Reports", Pract. Periodont Aesthet.Dent., (1998), 1107-1114 pgs.

* cited by examiner

SOFT TISSUE PRESERVATION TEMPORARY (SHELL) IMMEDIATE-IMPLANT ABUTMENT WITH BIOLOGICAL ACTIVE SURFACE

CROSS-REFERENCES TO RELATED APPLICATIONS

This is a continuation-in-part of application Ser. No. 13/655,056 filed Oct. 18, 2012, which was a continuation-in-part of application Ser. No. 13/356,359 filed Jan. 23, 2012 and now U.S. Pat. No. 8,425,231, and which are all incorporated herein by reference.

FIELD AND BACKGROUND OF THE INVENTION

The present invention relates generally to the field of dental implants and, in particular, to a new and useful soft-tissue preservation temporary in the form of a shell, with an immediate-implant abutment and a biologically active surface design that will promote soft-tissue attachment and adhesion according to the biologic and functional anatomic arrangement to the surface of the hollow-shell temporary abutment.

General Considerations and Problems to Overcome:

The tooth is a structure of the oral cavity which is vital to the capability of chewing and important to the general well-being and appearance of people. Anatomically, the tooth resides within the oral cavity, firmly anchored within the upper and lower jaws (maxilla and mandible). Human teeth reside within two distinct anatomic regions of the jaws; the apical inferior portion of the tooth (the root) is connected to the jaw via an attachment called the periodontal ligament. We will here define this portion of the tooth that is connected to the bone as the "bone-zone" or hard tissue zone of the tooth. Second, the superior portion of the tooth (the anatomic crown) is connected to the jaw in the soft-tissue or gingival region of the jaw defined as the "tissue-zone" or soft tissue zone. The anatomic crown is demarcated as that portion of the tooth superior to crest of bone and it will include a small portion of the root superior to the crest of bone as well as the clinical crown that is visible. The tissue-zone forms a soft-tissue collar around the neck of a tooth.

This tissue-zone connection (i.e. soft-tissue to tooth attachment) is composed of three basic anatomic structures of the dento-gingival fiber complex. They are defined as:

(1) the gingival sulcus that is lined by sulcular epithelium;
(2) the junctional epithelium; and
(3) the dento-gingival fibers (a.k.a., the gingival connective tissues).

The gingival sulcus is lined by the sulcular epithelium, a thin non-keratinized stratified squamous cell epithelium without rete pegs. The length of the sucular epithelium is 1 mm to 3 mm in height (on average 2 mm), and approximate the smooth surface of the enamel. The sulcular epithelium extends from the junctional epithelium to the crest of the soft-tissue free gingival margin. The sulcular epithelium is extremely important since it acts as the first line of defense from invasion of micro-organisms into the oral cavity. Maintenance and preservation of this structure is important. The sulcular epithelium acts as a semi-permeable membrane that keeps infecting bacteria by-products from migrating into the underlying connective tissue.

The junctional epithelium consists of a collar-like band of stratified squamous non-keratinized epithelium. It is three to four layers thick in early life but increases to 10 to 20 layers in later decades of life. The junctional epithelium is composed of two grouped states; the basal layer facing the connective tissue and the supra-basal layer extending to the surface of the tooth, creating an attachment/adherence to the enamel surface. The length of the junctional epithelium ranges from 0.25 mm to 1.35 mm (on average 1 mm) and a thickness of 10 to 29 cells wide to one or two cells in its apical termination, located at the cemento-enamel junction. The junctional epithelium is attached to the tooth surface (epithelial attachment) by means of an internal basal lamina to the unexposed enamel surface. It is attached to the gingival connective tissue by an external basal lamina that has the same structure as other epithelial-connective tissue attachments found elsewhere in the body.

The internal basal lamina of the junctional epithelium consists of lamina densa (adjacent to the enamel) and a lamina lucida to which hemidesmosomes are attached. Hemidesmosomes have a decisive role in the firm attachment of the cells to the internal basal lamina on the tooth surface. Hemidesmosomes may also act as specific sites of signal transduction and thus may participate in regulation of gene expression, cell proliferation, and cell differentiation. Hemidesmosomes attachment has been shown to occur on a textured surface. The attachment of the junctional epithelium to the tooth extends apical to the dento-gingival fibers, which produce a true functional attachment of collagen fibers to the surface of the tooth to the gingival connective tissue. All the structures thus far described (Sulcular Epithelium, Junctional Epithelium and the Dento-Gingival Fibers) are coronal or above (supra-crestal) to the bone.

The Dento-Gingival connective tissue is composed of dento-gingival fibers and connective tissue. The dento-gingival are composed of collagen fibers that surround the tooth on the facial, lingual and interproximal surfaces. The length of the supra-crestal dento-gingival fiber zone ranges from 1 mm to 3 mm and is on average 2 mm. The fibers are embedded in the surface of the root of the tooth that is coronal to the crest of bone. The supra-crestal dento-gingival fiber zone extends from the inferior aspect of the junctional epithelium to the superior aspect of the bone crest. The supra-crestal fibers that attach into the surface results from a cellular and an extracellular compartment composed of fibers and ground substance. The ground substance fills the space between the fibers and cells, is amorphous and has a high content of water. It is composed of proteoglycans, mainly hyaluronic acid and chondroitin sulfate, and glycoproteins, mainly fibronectin. The fibronectin binds fibroblasts to the fibers and to other components of the intercellular matrix, enabling cell adhesion and migration. Laminin, another glycoprotein found the connective tissue zone matrix serves to attach it to the surrounding cells. Three types of connective tissue fibers are found, collagen, reticular and elastic and are arranged with specific orientations to the surface of the tooth. The soft-tissue zone stability is established by the attachment of the fibers to the surface, this is a key factor to limiting the apical migration of the junctional epithelium. If the junctional epithelium was to migrate apically it would alter the functional attachment with negative outcomes as is seen during periodontal diseases. Therefore, re-establishing the dento-gingival zone of attachment is critical to the long-term stability and health of the dento-gingival complex (and soft-tissue zone).

With reference to FIG. 11, the three zones are described as Sulcular Epithelium 202, Junctional Epithelium 204, and the Dento-Gingival Fibers 206 and are noted about the parts of a natural tooth 102 with its root 104 in a bone socket 106 of a patient's jaw bone 112. The three zones 202, 204 and 206 are in a soft tissue socket 108 that will be left after tooth 102 is extracted. The soft tissue zones follow a peak and valley shape that mimics the scalloped contour of the free-gingival margin in gum or gingival 110 found around teeth. The peak and valley contour of the free-gingival margin is consistent with a peak and valley contour of the underlying bone around teeth when viewed from the buccal or lingual aspect. It is commonly understood that peak are higher (more coronal) between teeth and on the direct surface of the tooth the valley is (more apical). The differential between peak and valley is typically 3 mm to 6 mm depending upon the tooth under discussion. Anterior teeth display a greater peak to valley contour and posterior teeth display less of this peak to valley height. The peak to valley contour is commonly understood in dentistry as the "scallop" of the free gingival margin. Once again, the soft-tissue contour is reflective of the underlying bony shape and contour. The hollow shell herein described is designed with the naturally occurring peak to valley contour. Each zone described above follow the peak to valley contour on the natural tooth and therefore a hollow shell which is designed to preserve the anatomic configuration of the soft-tissue zone should provide a means to support and allow reattachment to each of these three soft-tissue zones described. The hollow shell herein disclosed provides a specific structure for each soft-tissue zone to enable reattachment/adhesion for that zone. Additionally and importantly each zone noted on the hollow shell is designed with a peak and valley configuration so that each given soft-tissue zone is matched to that zone found nature.

The soft tissue zone (or tissue zone) connection plays a critical role in maintaining health of the oral cavity. It does this by preventing the ingress of microbes and foreign substances into the body by providing a "biologic-seal" at the interface of the tooth-jaw connection at the tissue-zone through the adhesion/attachment of the sulcular epithelium, junctional epithelium and gingival fibers. This functional attachment of the soft-tissue to the surface of the tooth should be fully appreciated as a critical defense barrier. As without the presence of this soft-tissue biologic seal the underlying bone would be vulnerable to numerous invasions of various foreign substances.

In addition, the tissue-zone plays an essential role in maintaining and preserving the dental esthetics of the smile. This same tissue-zone represents the peaks (papillae) and valleys of the soft-tissue gingival that surround the neck of each and every tooth. These peaks and valleys have been defined for the hollow-shell temporary implant abutment herein referenced as our previous U.S. Pat. No. 8,425,231.

It is the spatial relationship of tooth form and color with healthy soft-tissue gingival architecture that are known as the essential building blocks of dental esthetics as we know it. Experts of dental esthetics have called the soft-tissue gingiva "the frame" of the picture, and regard the teeth as the "subject matter" of that painting. Disregarding the frame of a painting would certainly impact the overall esthetic appearance being viewed, and the same is true with respect to the gums and teeth. The loss or the alternation of anatomic structures of the tissue-zone has been shown to lead to an inferior esthetic outcome in addition to causing a potential risk of disease for the patient.

The tooth and its attachment to the jaw is subject to numerous pathogens over the lifetime of a patient, particularly due to trauma/fracture, endodontic failure, decay, localized periodontal disease, etc. Any of these conditions can lead to the eventual need for removal of either a single tooth or multiple teeth. The removal or extraction of a tooth or teeth will result in a radical morphologic change to the anatomy as well as the potential exposure of the internal tissues (connective tissues and underlying organs) of the body to invasion by foreign substances.

The extraction of a tooth results in a cascade of changes depending on how this procedure is performed. Tooth removal in the past has been a highly traumatic surgical procedure. It was not uncommon for an oral surgeon to fully reflect the gingival tissues as a surgical flap to expose the underlying tooth and bone to aid in the ease of access and visualization of the tooth to be removed. It is during this surgical reflection of the gingival soft-tissues that the normal anatomy of the tissue-zone would be radically altered and permanently changed. Destruction of the normal architecture of the gingiva occurs as surgical instruments were used to cut, tear, crush and rip the attachment fibers between the tooth and soft-tissues of the tissue-zone. In accordance with gingival surgical flap surgery, closure of a surgical flap is accomplished with the placement of sutures to close the wound created. Primary (or complete) flap closure is highly desirable to ensure the re-establishment of a biologic-seal of the soft-tissue to prevent ingress of foreign bodies to the host.

Gingival flap surgery also has the known deficiency to result in bone loss from the stripping away of the periosteum and hence the blood supply to the bone during the reflection of a surgical flap. It is well documented in the dental literature that gingival surgical flaps result in bone loss by the exposure of the underlying bone. Dr. Lindhe and co-workers have scientifically demonstrated that surgical flap elevation and removal of teeth leads to loss of the residual bone and the shape of remaining ridge after tooth removal. These undesirable anatomic changes to the bone make the placement of implants more complex and increases risk for patients.

For the reasons identified above, the trend toward minimally invasive surgical procedures has been developed toward the extraction of teeth. Examples of these changes include the use of micro-surgical instruments, periotomes and extraction forceps that do not require the reflection of a surgical flap to remove teeth. Ultrasonic (piezo technology) surgical instruments, dental lasers and rotary devices have been suggested as mechanisms to minimize trauma during the removal of teeth. It is generally accepted within the profession that a minimally invasive technique for tooth removal should be the standard of care.

In an attempt to minimize detrimental anatomic changes during the surgical removal of a tooth, a major effort is now underway to preserve the bone-zone and tissue-zone after tooth removal. The objective of the dental profession to preserve bone was a natural extension of a vast body of knowledge recently created on periodontal bone regeneration via the use of bone replacement substances. Examples of such efforts include autografts, allografts, xenografts and a variety of bone replacement materials that include; Bone Morphogenic Proteins (BMP's), Stem Cell Derivatives, Platelet Rich Proteins (PRP's) derived from the blood and numerous other biologic sources. Bone regeneration after periodontal disease is well established in the prior art. A deficiency of using bone replacement substances, are the inability to contain and protect these materials to exposure to the oral cavity during the critical healing phase, i.e. a fundamental inability to re-establish the all-important biologic-seal of the Tissue-Zone once a tooth is removed.

The use of barrier membranes for guided tissue bone regeneration (GTR) is known attempts to preserve and regenerate lost bone after periodontal disease. The use of membranes has more recently been applied to the regeneration and preservation of bone after tooth removal. Barrier membranes assist in creating a protective barricade to the bone-zone by excluding unwanted cells (connective tissue cells) to the healing site. This is an attempt to allow the body to more effectively refill a residual bony socket with bone cells (a.k.a. osteoblasts) known to be critical for bone growth. A general deficiency of using barrier membranes is the direct exposure of a barrier membrane that consequently lends to the inability to establish a soft-tissue seal. The exposure of the barrier membrane leads to plaque accumulation on the surface of the membrane that is impossible to clean. Once membranes become exposed to the oral environment, bacteria colonization on the surface of the membrane quickly spearheads an infection and/or failure of regeneration of bone. The primary cause of the exposure of the membrane is a lack of a soft-tissue biologic-seal after gingival flap surgery. The inability to re-establish a biologic-seal after the removal of a tooth has many repercussions to bone and soft tissue regeneration.

Loss of the biologic-seal of the tissue-zone also has a significant impact on soft-tissue changes to both the macro- and micro-anatomy of the gingiva. It is accepted in the dental literature that the loss of gingival attachment within the tissue-zone leads to the irreversible loss of the interdental papillae and the gingival architecture surrounding a tooth. There are currently no predictable surgical techniques available to correct the gingival changes to vertical height and horizontal dimensional after tooth removal. Much effort has been directed toward preserving the bone after tooth removal but far less effort has been applied to preserving the macro- and micro-anatomy of the tissue-zone after tooth removal.

As previously noted, the dento-gingival fiber complex plays a vital role in the protection of the host from foreign micro-organisms. The re-establishment of a biologic-seal that reconstitutes the macro- and micro-anatomy of the dentogingival complex is therefore essential to the long term maintenance of optimal health of the oral cavity and consequently the individual. Mechanical attachment of the underlying tissues to a tooth or abutment-implant tooth replacement within the tissue zone is facilitated by the cells of the dentogingival complex (sucular epithelium, junctional epithelium and gingival fibers).

A combination of focal points of adhesion contact, hemidesmosmal adherence/attachment and finite collagen fiber bundles, play a key role in the attachment interface. Histochemical evidence for the presence of neutral polysaccharides and the production of luminin provide an important contribution to the attachment interface at the level of the junctional epithelium. The gingival fiber attachment is composed of collagen fibers, fibroblasts, vessels, nerves and extra-cellular matrix. The bi-layer of the connective tissue; of the papillary layer subjacent to the epithelium and the reticular layer contiguous with the periosteum also contribute to a functional interface and hence the biologic seal found in the tissue zone. Maintenance of the attachment and/or adhesion of the soft tissue cells to the tooth surface are regulated via inter-cellular signaling (transduction) of the undifferentiated and differentiated cells, such as fibroblasts, cementoblasts, endothelial cells, as well as, the hemidesmosmal cells of the soft tissues.

As will be explained more fully in the following, the new method and arrangement of the present invention is an effective means to preserve anatomic architecture of the tissue-zone after tooth removal and a means to re-establish the adherence and attachment of the adjacent soft tissue via a biologic seal at the time of an immediate placement of a dental implant. In addition, the present invention describes a means of providing a biologic surface onto an abutment to which the biologic seal is promoted and can be re-established.

The understanding of using a minimally invasive technique as well as re-establishing a biologic-seal after tooth removal has been discussed but has not yet been made possible in all cases by known methods and apparatuses. In addition to these important concepts one further concept related to tooth removal is the technique of immediate dental implant placement after the extraction of a tooth/teeth and the ability to provide a surface texture, surface or biologically active layer upon the surface to promote re-establishment or new attachment/adhesion to the surface of the implant abutment.

The replacement of a tooth by a dental implant device is well known in the prior art. It is understood that there are two basic components to the dental implant device; the root-form component held within the bone-zone commonly referred to as the "dental implant" and a second component, the implant anatomic crown composed of an abutment and clinical crown. Both the abutment and clinical crown are typically placed superior to the crest of bone therefore within and superior to the tissue-zone. An implant prosthesis was first described as a surgical method and device that used a fully submerged, non-loaded healing period prior to the connection of the dental implant crown.

The advent of contemporary implant dentistry was first described by Prof. P. I. Branemark in the late 1970's and established the use of a titanium root-form screw to be inserted into the bone placed by using an atraumatic surgical technique described by this researcher/inventor. The method described by Branemark discussed the placement of the dental implant into jawbone of a fully edentulous ridge. He described a method in which the implant would be fully submerged and non-loaded during a healing period of 4-6 months after the dental implant was placed and covered within the bone. Pre-operative conditions therefore required a fully healed ridge in which teeth were previously removed. The method of using a submerged, non-loaded healing period for dental implants remains an approach still widely utilized today.

However, over the past 30 years alternative methods to implant placement have occurred. The following are different methods that have been advocated to the non-submerged, non-loaded implant healing technique.

Advantages and disadvantages will be briefly discussed for each technique.

Delayed, Submerged, Non-loaded Implant Placement Method:

Defined as the method for placing a root-form dental implant into the jawbone. The implant is placed within the bone-zone initially. The pre-operative condition requires an edentulous ridge. The technique describes the placement of the implant into the bone at or below the crest of bone and it is fully covered by primary flap closure. An initial healing for a period of 4 to 6 months is required. A second surgery is required to expose the root-form implant and to connect a healing abutment. Second healing period of 2-3 months is required for soft-tissue. Final crown delivery occurs approximately 9 months after the start of treatment.

Deficiencies of this Method:

1. Requires multiple surgeries prior to implant crown placement.

2. Requires an edentulous ridge prior to implant placement into the bone-zone resulting in the irreversible changes to the soft-tissues of the tissue-zone.

3. Difficult to re-establish a biologic-seal after numerous surgeries and the connection of the implant crown.

4. Increased cost because of multiple surgeries and prosthetic components.

5. Previous implant system provided a bone-zone solution to osseo-integration of a root form implant within the bone. These systems were not designed with a separate component that is devised to re-establish the soft-tissue zone connection in the immediate implant placement.

6. Does not provide a suitable surface adjacent to the host soft-tissue zone (dentogingival complex) to promote or re-establish a biologic seal during the extraction and immediate implant placement.

Delayed, Non-submerged, Non-loaded Implant Placement Method:

Defined as the method for placing a root-form dental implant into the jawbone exemplified by the Straumann, ITI implant company. The implant is placed within the bone-zone initially. The pre-operative condition requires an edentulous ridge. The technique describes the placement of the implant into the bone at or below the crest of bone or within the tissue-zone. A transmucosal healing cap component is used. A healing abutment or "cap" is placed onto the implant that is in direct contact with the soft-tissue during the initial bone-healing period of 4 to 6 months. A second surgery is not required to expose the root-form implant. Reformation of the tissue-zone is required. A connection between the implant and the healing abutment is within the tissue-zone.

Deficiencies of this Method:

1. Requires an edentulous ridge prior to implant placement into the bone resulting in the irreversible changes to the soft-tissues of the Tissue-Zone.

2. Requires flap surgery to place dental implant.

3. Difficult to re-establish a biologic-seal after surgery and the connection of the implant crown.

4. Difficult to re-establish soft-tissue anatomy to the state it was prior to tooth removal.

5. Healing abutment has a connection interface within the Tissue-Zone, which allows bacteria to adhere impeding wound healing.

6. Increased cost because of multiple components.

7. Does not provide a means to maintain the original soft tissue architecture while affording a suitable surface for re-attachment at the time of tooth removal and immediate implant placement.

Immediate Root-form Implant Placement:

A recent trend in implant dentistry that has occurred, that overcomes the deficiency of requiring multiple surgeries, is the immediate placement of a root-form dental implant directly into an extraction socket after tooth removal.

This method deviates from the original protocols established by Branemark and co-workers. The advantage to the simultaneous placement of a root-form dental implant after tooth removal is the reduction of the number of clinical procedures required as well as decreased treatment time. This technique eliminates the need to have the bone ridge healed after tooth removal consequently requiring fewer surgical procedures.

Immediate implant placement requires a mechanical locking of the root-form dental implant into the residual socket-site after a tooth has been removed. Mechanical locking refers to the root-form implant engaging undisturbed bone in an attempt to provide primary mechanical stability of the implant within the extraction socket. Immediate implant placement is highly desirable in comparison to delayed implant placement since it allows the immediate replacement of the tooth at a substantially reduced amount of time when compared to previous method of delayed implant healing.

Immediate Implant Placement Presents Numerous Risks and Deficiencies with Current Methods Used:

1. An inability to fully engage the entire remaining socket surface after tooth removal, thereby leaving a space (gap) between the surface of the implant and the surface of the remaining bone.

2. An inability to establish a biologic-seal to the overlying soft-tissues after a tooth has been removed.

3. An inability to retain bone regenerative materials if a residual gap remains between the surface of the implant and the bone socket.

4. An inability to establish a biologic-seal of the soft-tissue over a barrier membrane to protect and contain bone regeneration materials and the blood clot.

5. Inability to preserve the soft-tissue architecture of the gingival of the Tissue-Zone.

6. Inability to promote and/or re-establish a cellular and soft-tissue attachment and/or adherence of the adjacent soft-tissue zone defined as the dentogingival complex to the surface of the an immediate implant abutment.

The deficiencies of achieving a predictable and esthetic long term outcome when using an immediate implant placement protocol can all be directly attributed to the inability to establish an acceptable soft-tissue adaptation that creates an effective biologic-seal, one which re-establishes a true histological and biochemical attachment in the tissue-zone of the remaining soft-tissue socket after removal of a tooth.

Immediate implant placement of a root-form dental implant has been shown to effectively osseointegrate by numerous authors (reference included herein). The residual gap that is present between the implant surface and the bone surface requires careful management whether a surgical flap is performed or a non-flapless minimally invasive extraction technique is used. In either of these two approaches, irreversible soft-tissue changes have been shown to occur with immediate implant placement after tooth removal. Changes within the tissue-zone are shown to occur as early as several hours to more extensive changes over several days after the immediate implant placement.

Numerous authors (reference included herein) have discussed the use of a biologically active surface and the importance of a soft tissue attachment of a medical (dental) implants (e.g., stents, dental implants, canulas and the like). Areva, et. al. (2004, J Biomed Mater Res., 70A: 169-178) described the use of a non-resorbable reactive tetraisopropyl orthotitanate layer (i.e., sol-gel derived nano-porous titainia coating) dissolved in absolute ethanol. A second solution of Ethyleneglycol monoethylether deionized water and fuming hydrochloric acid (HCL, 37%) dissolved in ethanol. The two solutions are mixed and aged for 24 hours and used as a dip-coating process on a titanium substrate. The detailed process described by Areva and co-workers as a "sol-gel derived titania coating" used to produce a soft tissue attachment. Their histo-morphological and chemical analysis using scanning electron microscope equipment demonstrated a good adherence and direct soft tissue attachment of the treated surface.

Rossi, et. al., in a subsequent publication (Peri-Implant tissue response to TiOxide surface modified implants. Clin Oral Impl Res. 19, 348-355, 2008) described the use of a TiOxide thin film layer applied to a smooth implant surface promoting a hemidesmosome attachment. This animal study demonstrated histological and histomorphometric arrangements of the sucular epithelium, junctional epithelium and gingival fibers with direct contact and attachment to the surface of the implant when treated with a thin film TiOxide applied layer. Within the limitations of this study it can be concluded that a non-porous TiOxide surface offers good soft tissue attachment around root form implants.

In addition to the application of a biologically active surface noted above, numerous researchers have discussed the benefits of altering surface properties of an implants with respect to the micro- and macro-morphology of the surface of implants to promote attachment to the implant surface. Such examples relate to laser etching, roughness and texture. Ricci and co-workers (Key Engineering Materials, Vols 198-199; 179-202.2001) describe the effects of textured surfaces on colony formation by fibroblasts and effects of controlled surface micro-geometries. Based on this research a laser micro-grooved surface was tested. Specific size ranges were applied producing a controlled micro-geometry to enhance bone and soft tissue integration. Subsequent studies by this team lead to the development of a patented laser micro-grooving surface morphology (U.S. Pat. No. 6,419,491 herein referenced). Laser micro-grooving surface texture has demonstrated increased soft tissue adhesion and attachment to the surface of titanium dental implants. Other surface characteristics such as hydrophilicity and the use of depositing non-toxic salt residue on a roughened surface of the implant has been described (U.S. Pat. No. 8,309,162 to Charlton, et. al.). Charlton and co-workers described an acid-etched roughened surface with an array of microscale irregularities having peak-to-valley heights not greater than 20 microns. A method of applying discrete hydroxyapatite nano-crystals on the roughened surface exposed to a solution comprising non-toxic salts to promote cell attachment is disclosed. In the same patent, a method of increasing the hydrophilicity by depositing a non-toxic sodium lactate salt residue on the surface of a dental implant to be implanted into living bone promoting improved osseo-integration (cellular attachment) is claimed and described.

Liu, et. al, U.S. Pat. No. 7,341,756 describe applying a multi-layer derived alkoxide on a substrate having a dimension suitable for an implant and forming a second coating layer on the first coating layer that promotes osseointegration. The patent further describes the multi-layer surface applies sol-gel processing to produce a nanometer scale of calcium phosphate (e.g., HA) ultrathin-coating. The bioactive surface of the multi-layer surface coating accelerated osteoblast adhesion and may generate improved osseo-integration of implants within bone. Results of such a surface coating indicted that genes associated with bone formation (col1, OPN, OCN) were unregulated with the multi-layer surface described.

Other Prior Art:

U.S. Pat. No. 5,417,568 to Giglio discloses a dental prosthesis that is said to accommodate the gingival contours surrounding the implant prosthesis by imitating the gingival contours around natural teeth. Since the abutment is rigidly connected to the implant and must always be axially aligned with the long axis of the implant, the abutment will rarely, if ever, closely engage the entire existing soft-tissue socket created when a tooth has been extracted; consequently, inadequate soft tissue socket adaptation exists. Moreover, seldom is the axis of the implant exactly aligned with the axis of the soft-tissue socket. Also, although the abutment disclosed by this patent has raised ridges around its outer perimeter, it is symmetrical, and therefore does not mimic the asymmetric anatomy of a soft-tissue socket in the gingiva of a patient from whom a tooth has been extracted.

Nowhere in the prior art or in current dental implant wisdom is an anatomically shaped and sized abutment in the form of a hollow, asymmetric tubular shell used in conjunction with a dental implant, which is not rigidly or concentrically connected to the implant in advance. As a result of the invention here disclosed, the shell can be moved and maneuvered to any orientation in the x-, y- or z-axis in a soft-tissue socket to effectively and fully engage the tissue-zone with no space or gap between the outer surface of the shell and the soft-tissue socket, independent of the position and axial orientation of the implant in the bony socket. The mechanical de-coupling of the abutment shell from the implant is one of several important advancements of this invention over the prior art.

U.S. RE37,227 to Brodbeck also disclosed a some-what anatomically shaped abutment but again it is axially fixed to an implant so that there is no freedom of movement between the abutment and the implant but rather they are mechanically coupled to each other when being seated in their respective soft-tissue and bone sockets.

An article titled: "*Immediate Placement and Provisionalization of Maxillary Anterior Single Implants: A Surgical and Prosthodontic Rationale,*" by Kan at al., Pract Periodont Aesthet Dent, 2000; Vol. 12, No. 9, pps 817-824, discloses the building up of an abutment that is fixed to an implant to better match a soft-tissue socket by the addition of autopolymerizing acrylic resin around the abutment by sculpting the outer shape of the otherwise fixed abutment to better fill the soft-tissue socket. This technique also fails to recognize the advantage of mechanically decoupling the abutment from the implant. In addition, the tissue-zone collapses immediately upon tooth removal and extrapolation of its contours by the author is required to recreate as close as possible the soft tissue-zone profile.

Nowhere in the prior art or in current dental implant wisdom is an anatomically shaped and sized abutment in the form of a hollow, asymmetric tubular shell in which a biologically active surface consisting of, but not limited to, surface texture, surface roughness, hydrophilic surface, surface conditioning by applying bio-active agents, creating of a macro- and micro-geometric pattern and/or micro- and macro-morphology surface irregularities (as those previously referenced and described above) to promote the soft-tissue attachment and/or adhesion of the dentogingival complex within the tissue-zone of an immediately placed implant abutment which is capable of making contact with the entire soft-tissue socket when placed upon the immediate implant of the extracted tooth site.

Nowhere in the prior art is a discussion or apparatus that allows a biologically active surface as described above to have intimate contact with the exposed soft-tissue socket immediately after tooth removal and is capable of compensating for eccentric positioning of the dental implant secured within the bone. The apparatus thus provides a means to allow immediate cellular activity from physical contact of the apparatus surface to the direct contact of the soft-tissue surface without the presence of a gap. Additionally, the biologic mediators described above are thus capable of promoting a direct soft-tissue attachment and/or adherence of the implant abutment to the immediate soft-tissue residual socket of the extraction tooth.

Another attempt at accommodating the miss-match between an implant oriented in a bony socket and an abutment positioned in a soft-tissue socket, is suggested in the June 2009 brochure of BIOMET 3i titled "*Ideal Solutions For Immediate Aesthetics*" that discloses an abutment-implant combination where the abutment axis is at a fixed but non-aligned angle to the implant axis. Here again there is no decoupling of the abutment from the implant so freedom of orientation is not present. Nor is there the suggestion of a biologically active surface that can promote re-attachment of the soft-tissue to the surface of the abutment-implant.

SUMMARY OF THE INVENTION

The present invention seeks to establish a biologic active surface that is achieved by coating, applying or conditioning the surface of our temporary shell of the invention. We disclose a surface that may be coated by an organic or inorganic surface layer to promote and/or achieve a biological and anatomic connection of the cells of the soft-tissues to the surface of the shell. Thus, promoting and establishing the optimal soft tissue gingival seal.

A major advantage of the invention is that the structure of the hollow shell makes intimate contact with the entire surface of the soft-tissue socket at the time the extraction is performed. The hollow shell comes into direct contact along the entire surface of the shell with a biologically active agent to promote soft-tissue re-attachment and/or adherence.

Providing a biologic or biologically active agent at the time of tooth removal is different then at any other time. Wound healing cells and mechanisms are temporal and having them present with a direct contact to the biological active agent on the surface of the hollow shell is a unique circumstance of this invention.

It is an object of the present invention to solve the problems of the prior art by providing a soft-tissue preservation, dental implant arrangement, that comprises: a hollow shell with an interior volume and a shell axis, the hollow shell having an outer bio-compatible surface for engaging a soft-tissue socket that is left in gingival tissue after a tooth has been extracted from a bone socket under the gingival tissue, the shell having a first perimeter adapted for placement toward the bone socket and a second perimeter adapted for placement adjacent an outer surface of the gingival tissue around the soft-tissue socket, the first perimeter being smaller than the second perimeter so that the shell tapers outwardly from the first to the second perimeters, the second perimeter being asymmetrically scalloped with opposite distal and mesial peaks and opposite lingual and facial valleys between the peaks, and the shell being sized for closely engaging against the soft-tissue socket without gaps; a dental implant having an implant axis and being adapted for placement in the bone socket; a temporary post rigidly connected to and coaxial with the dental implant, the temporary post extending in the interior volume of the hollow shell; and a luting compound filling the interior volume between the shell and the temporary post and setting solid for fixing the shell to the dental implant with no other connection between the shell and the implant so that the outer surface of the shell engages against the soft-tissue socket without gaps and without requiring alignment of the shell axis to the implant axes.

The above described hollow shell to be composed of a bio-active outer surface that is defined by but not limited to, a particular surface texture, surface roughness, hydropholic surface, surface conditioning by applying bio-active agents, creation of a macro- and micro-geometric pattern and/or micro- and macro-morphological surface irregularities (as those previously referenced and described above) to promote soft tissue attachment and/or adhesion of the dentogingival complex. The biologically active surface of the hollow shell is to make direct and intimate contact about the entire surface with the "fresh" soft-tissue socket and peri-implant tissues of the extracted tooth. The hollow shell with bioactive surface interacts with the exposed soft-tissues at the time of the removal of the tooth. This condition is unique in time and space. It is known that wound healing is a cascade of cellular responses that occur and only occur at specific times that are in relation to the traumatic event within time. The removal of a tooth starts this cascade of wound healing events by exposing the "fresh" surface of the soft-tissue after tooth removal. There is a distinct advantage for wound healing that is enabled at a specific time thus allowing the biologically active surface to be in intimate and immediate contact to the soft-tissue at the time of tooth removal. This condition is one that is temporal and is unique to the method herein described in which a biologically active surface can comes into intimate and direct contact with the "fresh" soft-tissue socket to promote the re-attachment and/or direct chemical adherence of this surface to the newly exposed soft-tissue.

The preferred embodiment of this method and apparatus are specific to the immediate extraction site and placement of the immediate implant and overlying immediate implant abutment. The inventor's clinical experience and case studies have shown that allowing a biologically active surface of the hollow shell to be in contact with the immediate and "fresh" soft-tissue extraction site enables a cascade of wound healing that is not present under any other conditions. This has resulted with the ability to demonstrate tissue attachment and true adherence typically only found prior to tooth removal.

In the preferred embodiment the invention provides a textured and coated outer surface of the hollow shell composed of three distinct zones corresponding to those shown FIG. 11. Each zone is designed with the peak and valley contour arrangement that parallels the upper (coronal) edge of the hollow shell. This peak and valley contour is consistent with the three zone that were previously described relating to the sulcular epithelium, junctional epithelium and dento-gingival fiber zone, respectively found juxtaposing a tooth. In the preferred embodiment, the most upper (coronal) of the three zones is the sulcular epithelium zone that is designed to be 2 mm in height. The middle zone on the hollow shell which approximates the junctional epithelium zone is designed to be 1 mm in height and the third zone, the bottom (apical) zone which will approximate the dento-gingival fibers of the connective tissue is designed to be 2 mm in height on the surface of the hollow shell.

A lower (apical) zone of the hollow shell is textured with a pitted-roughened surface with a diameter of 25 to 50 microns and 5 to 10 microns in depth for the surface texture. The height of the zone is 2 mm and will approximate the dento-gingival connective tissue and fibers of the residual soft-tissue zone. This band of the hollow shell corresponds to the surface of the tooth in which the dentogingival fibers insert on the surface of the tooth. It is conceivable that this zone of the hollow shell is coated with a biologically active agent that produces proteoglycans and cementogenesis to further encourage the dento-gingival fibers to insert into the surface. It is understood that the surfaces of the hollow shell are not limited to three distinct zones and could be one or more zones of any of the surface textures described. It is understood that each zone (band) of the hollow shell will follow the contour of the upper (coronal) edge of the hollow shell structure with a peak and valley shape reflective of the soft-tissue zone.

A further and more general object of the invention is to provide a dental implant method and arrangement that uses a hollow shell with outer bio-compatible surface for engaging a soft-tissue socket that is left in gingival tissue after a tooth has been extracted to promote healing by mechanically decoupling the shell from an implant that has been fixed in the remaining bony socket, the shell being tapered outwardly from a first to a second perimeter, the second perimeter being asymmetrically scalloped with opposite distal and mesial peaks and opposite lingual and facial valleys between the peaks, the dental implant in the bone or bony socket left after tooth extraction being rigidly connected to a temporary post, the temporary post extending in the shell and a luting compound filling the volume between the shell and the post and setting solid for fixing the shell to the dental implant with no other connection between the shell and the implant so that the outer surface of the shell engages against the soft-tissue socket without gaps and without requiring alignment of the shell and implant axes.

Another object of the invention are to use the shell as a biological seal enhanced and promoted through the use of a biologically active surface for both the soft-tissue socket and for the bony socket, to preclude contaminants from the soft-tissue and from the bony sockets. The biologically active agents may also retard the growth of opportunistic pathogens at the interface. Namely, the addition of a biologically active surface may also prevent the colonization of bacteria and the like as well as reduce the inflammatory reaction typically associated with host challenges. We anticipate that a biologically active surface is also a surface that is defined to prevent specific cellular proliferation and adverse outcomes. It is conceived that the use of a biologically active surface includes a particular surface texture, surface roughness, hydrophilic surface, surface conditioning, macro- and micro-geometric pattern and/or micro- and macro-morphological surface irregularities (as those previously referenced and described above) to promote and prevent specific cell populations from soft tissue attachment and/or adherence. An example of this concept would be a biologically active surface that will prevent the apical (downward) migration of sucular epithelium onto the entire surface of the hollow shell. A further example would be a biologically active surface that will prevent an apical migration of the Junctional Epithelium onto the surface of an immediate implant abutment that would otherwise be an area with dentogingival fiber attachment. In conclusion, the hollow shell with a biologically active surface is capable of controlling selective cellular repopulation along its surface thereby promoting a true re-attachment and/or adherence of the immediate soft-tissue extraction site.

The present invention also includes another important concept that the biologically active surface can also prevent undesirable cellular attachment and/or adhesion in addition to the general concept of preserving and promoting re-attachment.

Another object of the invention is to use the shell as a foundation for a temporary prosthetic tooth for immediately cosmetically replacing an extracted tooth.

Other objects of the invention will become apparent after considering the following more detailed disclosure of the invention.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
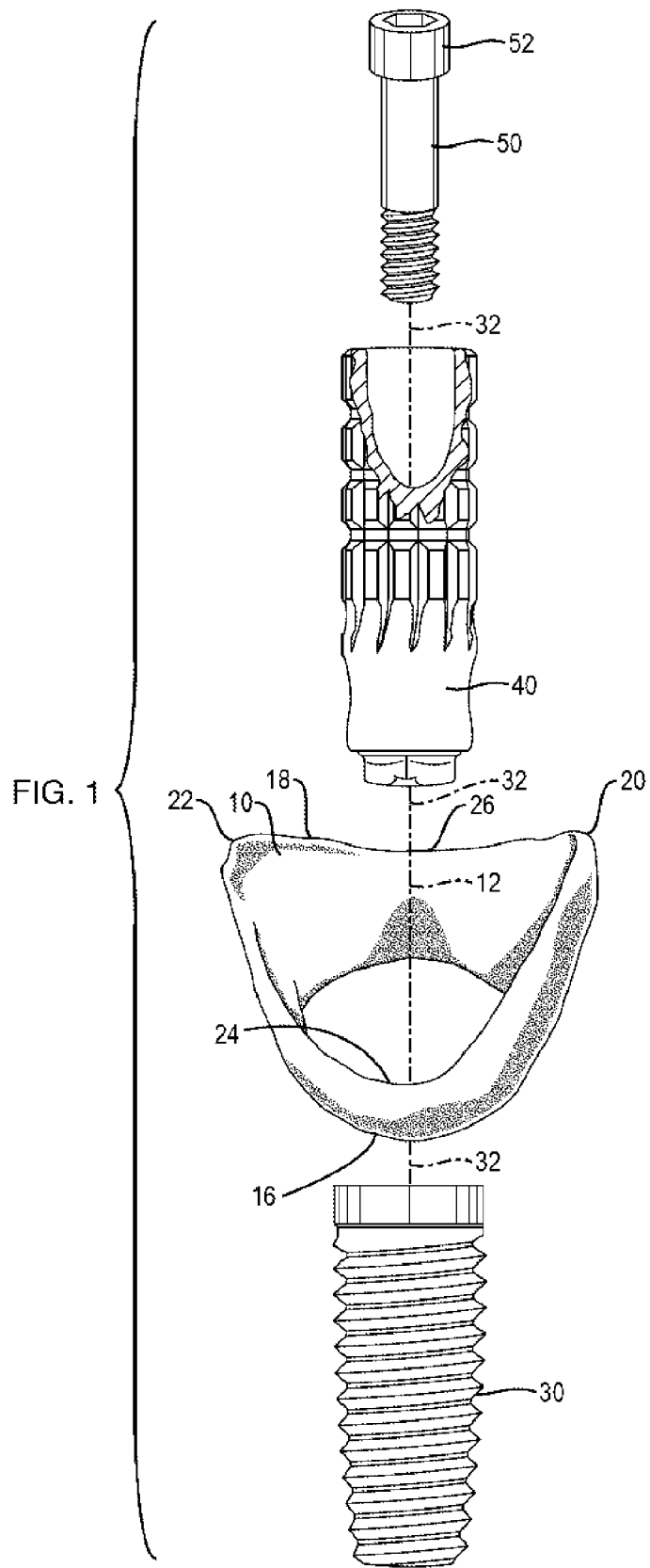
FIG. 1 is an exploded view of important part of the arrangement of the invention.

Referring now to the drawings, in which like reference numerals are used to refer to the same or similar elements, FIG. 1 illustrates a soft tissue preservation, dental implant arrangement, that comprises a hollow shell 10 with an interior volume and a shell axis 12. The shell is advantageously made of zirconium dioxide ($ZrO_2$) ceramic material that is known to be bio-compatible. The hollow shell 10 thus has an outer bio-compatible surface for engaging a soft-tissue socket that is left in gingival tissue after a tooth has been extracted from a bone or bony socket under the gingival tissue. Shell 10 has a first lower perimeter 16 adapted for placement toward the bone socket of a lower mandibular, tooth. The first or inner perimeter 16 may be an upper perimeter if the shell is to be used for replacing of an extracted upper or maxillary tooth so that terms like "upper" and "lower" as used here are only relative terms and do not convey an absolute position or limitation of the invention.

Shell 10 also has a second or outer perimeter 18 adapted for placement adjacent an outer surface of the gingival tissue, around the soft-tissue socket. The first perimeter 16 is smaller than the second perimeter 18 so that the shell 10 tapers outwardly from the first to the second perimeters to anatomically mimic the shape of the soft-tissue socket that remains immediately after a tooth has been extracted, and before the soft-tissue socket starts to shrink or shift from the natural size, shape and position it had around the patient's natural tooth before extraction.

To further anatomically mimic the shape of the soft-tissue socket, the second perimeter 18 is also asymmetrically scalloped with opposite distal and mesial peaks 20 and 22, and opposite lingual and facial valleys 24 and 26, between the peaks. The shapes, sizes, locations and heights of the peaks and valleys are selected to mimic known tooth types, e.g. maxillary or mandibular, central or lateral incisors, canines, premolars and molars, and the shell is also sized for closely engaging against the soft-tissue socket without gaps of many tooth shapes, types and sizes. This sizing and shaping is achieved by providing the practitioner with a set or selection of different shell shapes, sizes and types, so that a shell 10 that is close in fit to the soft-tissue socket is available, so that the shell engages the soft-tissue socket without gaps and thus forms a biological or biologic-seal to preclude contaminants from the soft-tissue socket and from the bony socket in the bone under the soft tissue.

Figure 2:
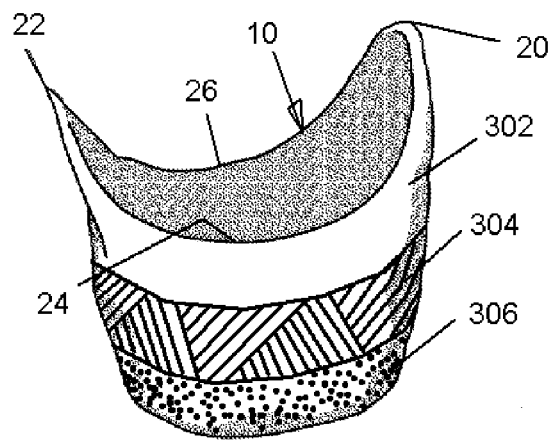
FIG. 2 is a perspective view of a different embodiment of the shell of the invention for use in replacing a different tooth type and illustrating the outer zones of different surface type of the invention.
Figure 12:
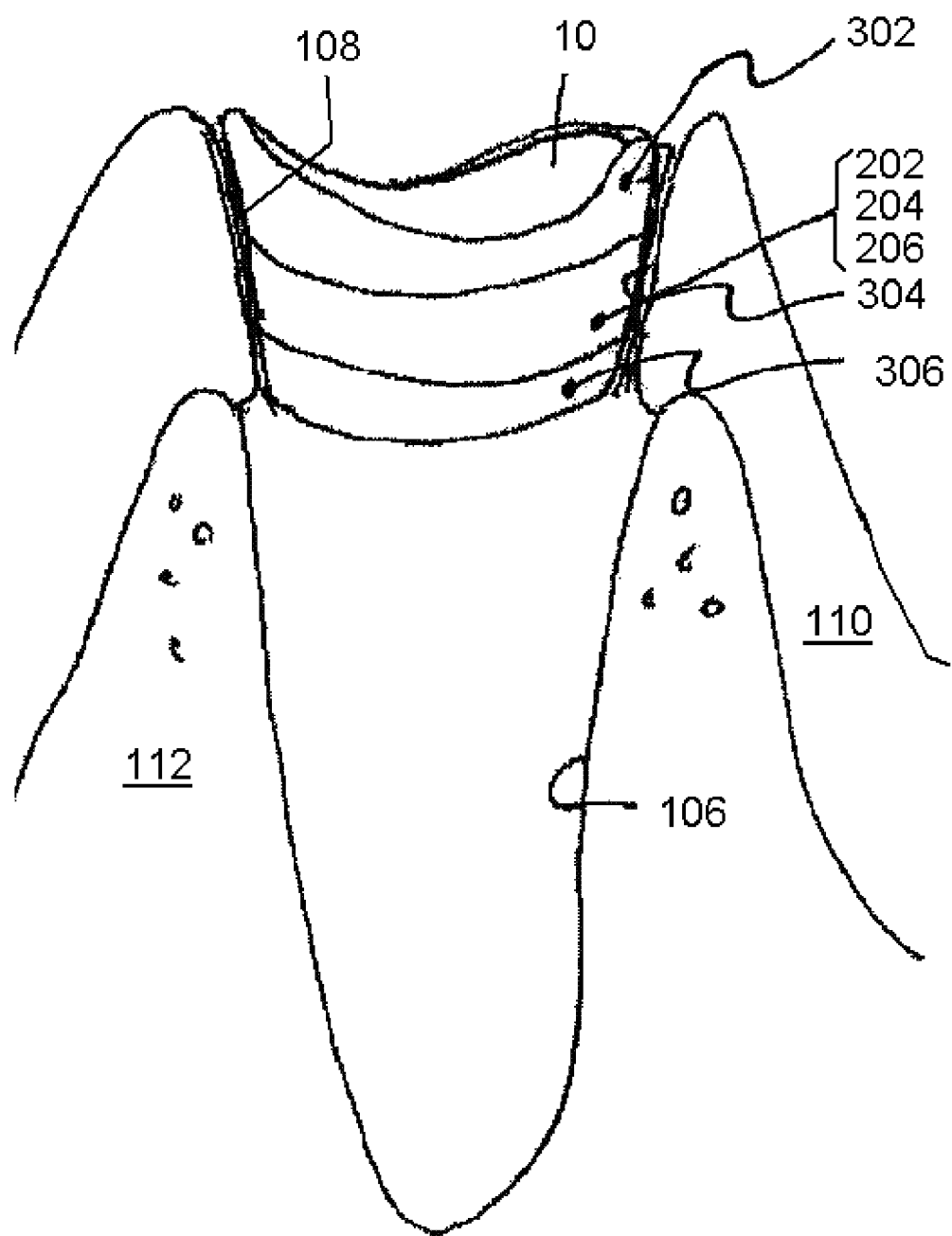
FIG. 12 is side sectional view of a shell of the invention in soft tissue socket after a tooth has been extracted to illustrate the invention.

According to the invention as shown in FIG. 2, the outer surface if shell 10 is divided into at least two and preferably the zones 302, 304 and 306 corresponding to the gingival sulcus (202), junctional epithelium (204) and dento-gingival fiber (206) zones of the natural soft tissue socket shown in FIG. 12 at 108 in the gingiva 110.

One or more biologically active agents, such as but not limited to, a particular surface texture like macro-grooves are provided in zone 304, surface roughness, hydrophilic surface, surface conditioning or applying bio-active agents of a different type are on the surface of shell 10 in zone 306, and zone 302 is left smooth. Alternatively creating of a macro- and micro-geometric pattern and/or micro- and macro-morphological surface irregularities (as those previously referenced and described above) are applied to the different zones 302, 304 and 306, to make best biocompatible contact with the respective zones 202, 204 and 206 of the soft tissue socket and further enhance preservation of the anatomy of the socket in preparation for its eventual engagement by a crown or permanent tooth replacement that will replace the shell 10.

In conjunction with an immediate implant technique of the invention, and by using the inventive multi-zone shell 10, the soft tissue socket experiences the least amount of trauma.

Figure 11:
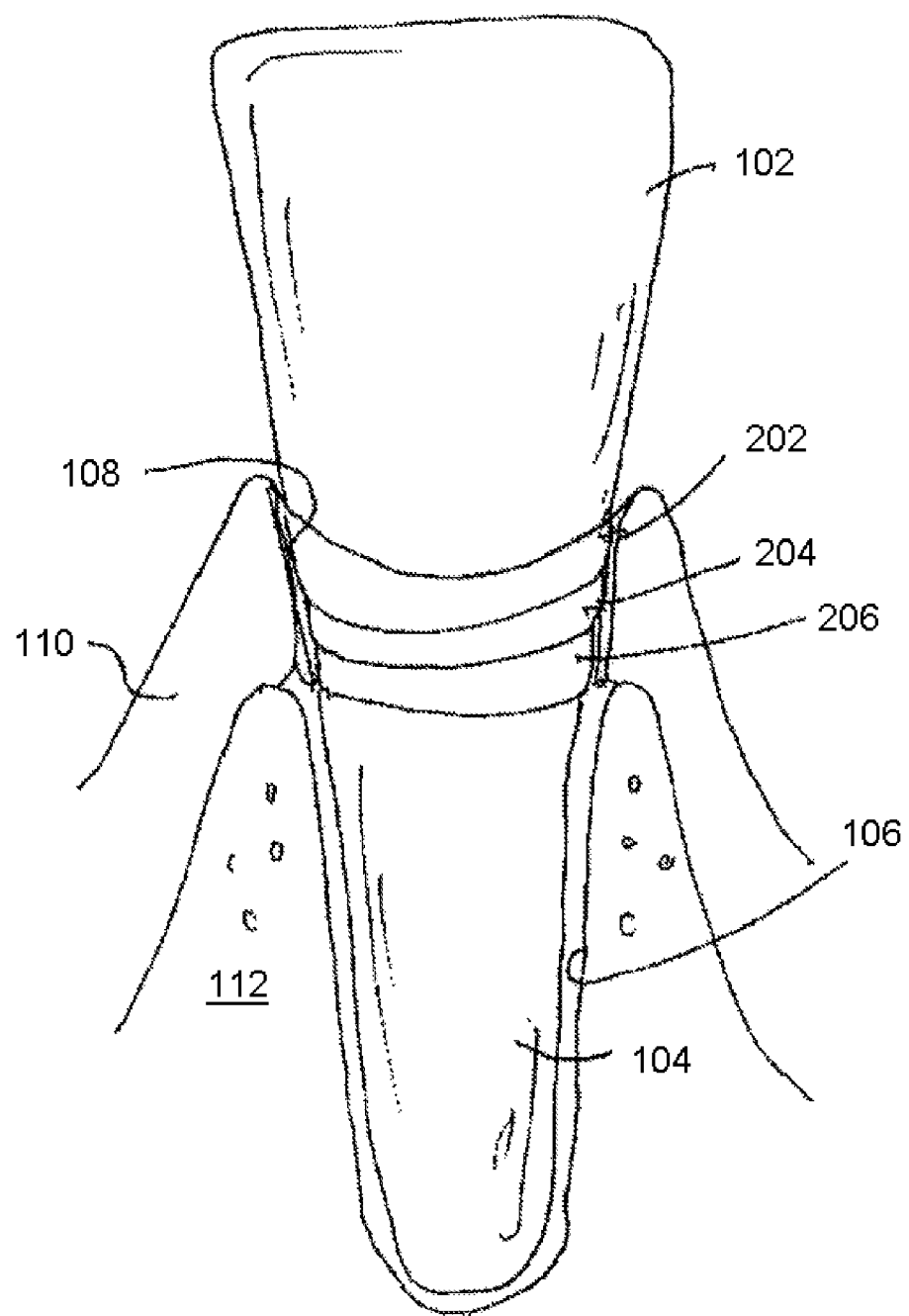
FIG. 11 is side sectional view of a natural tooth in a human jaw to illustrate key areas of the anatomy of the tooth and its surroundings for a better understanding of the invention.

In greater detail, the preferred embodiment the invention provides a textured and coated outer surface of the hollow shell 10 composed of three distinct zones, namely a third zone or band 302, a second zone or 304 and a third zone or band 306 in FIGS. 2 and 12, corresponding to the soft tissue zones 202, 204 and 206 shown in FIGS. 11 and 12.

Each zone is designed with the peak and valley contour arrangement that parallels the upper (coronal) edge of the hollow shell. This peak and valley contour is consistent with the three zones that were previously described relating to the sulcular epithelium, junctional epithelium and dento-gingival fiber zone, respectively found juxtaposing a tooth. In the preferred embodiment, the most upper (coronal) of the three zones is the sulcular epithelium zone that is designed to be 2 mm in height. The middle zone on the hollow shell which approximates the junctional epithelium zone is designed to be 1 mm in height and the third zone, the bottom (apical) zone which will approximate the dento-gingival fibers of the connective tissue is designed to be 2 mm in height on the surface of the hollow shell. Each zone on the hollow shell is designed to promote the cell specific type of attachment, which is found against the natural tooth surface. The most upper (coronal) zone of the hollow shell is a smooth, non-textured surface, (FIG. 2, 302) which will inhibit plaque adherence to the surface. It is conceivable that this surface will be coated with an anti-microbial agent such as silver or a hydrophobic agent to repel bacteria contact. The middle zone (band) of the hollow shell is textured with vertical and oblique grooves (FIG. 2, 304) that follow the peak to valley configuration of the two other zones described. The grooves are separated by a distance between 5-7 microns and are a depth of 10-20 microns. This textured zone is 1 mm in height. A vertical and oblique grooves form a band that in circles the perimeter of the hollow shell with a peak and valley contour mimicking the upper (coronal) edge of the hollow shell and this surface approximates the junctional epithelium of the soft tissue socket and it has been found to encourage the hemidesmosomal attachment of the junctional epithelium. It is conceivable that a biologic agent, which layers a sol-gel application as noted in this document to establish adhesion/attachment of the junctional epithelium, is anticipated.

The lower (apical) zone of the hollow shell is textured (FIG. 2, 306) with a pitted-roughened surface with a diameter of 25 to 50 microns and 5 to 10 microns in depth for the surface texture. The height of the zone is 2 mm and will approximate the dento-gingival connective tissue and fibers of the residual soft-tissue zone. This band of the hollow shell corresponds the surface of the tooth (FIG. 11, 206) in which the dentogingival fibers insert on the surface of the tooth. It is conceivable that this zone of the hollow shell is coated with a biologically active agent that produces proteoglycans and cementogenesis to further encourage the dento-gingival fibers to insert into the surface. It is understood that the surfaces of the hollow shell are not limited to three distinct zones and could be one or more zones of any of the surface textures described. It is understood that each zone (band) of the hollow shell will follow the contour of the upper (coronal) edge of the hollow shell structure with a peak and valley shape reflective of the soft-tissue zone.

A further and more general object of the invention is to provide a dental implant method and arrangement that uses a hollow shell with outer bio-compatible surface for engaging a soft-tissue socket that is left in gingival tissue after a tooth has been extracted to promote healing by mechanically decoupling the shell from an implant that has been fixed in the remaining bony socket, the shell being tapered outwardly from a first to a second perimeter, the second perimeter being asymmetrically scalloped with opposite distal and mesial peaks and opposite lingual and facial valleys between the peaks, the dental implant in the bone or bony socket left after tooth extraction being rigidly connected to a temporary post, the temporary post extending in the shell and a luting compound filling the volume between the shell and the post and setting solid for fixing the shell to the dental implant with no other connection between the shell and the implant so that the outer surface of the shell engages against the soft-tissue socket without gaps and without requiring alignment of the shell and implant axes.

The invention uses the shell as a biological seal enhanced and promoted through the use of a biologically active surface for both the soft-tissue socket and for the bony socket, to preclude contaminants from the soft-tissue and from the bony sockets. The biologically active agents may also retard the growth of opportunistic pathogens at the interface. Namely, the addition of a biologically active surface may also prevent the colonization of bacteria and the like as well as reduce the inflammatory reaction typically associated with host challenges. We anticipate that a biologically active surface is also a surface that is defined to prevent specific cellular proliferation and adverse outcomes. It is conceived that the use of a biologically active surface includes a particular surface texture, surface roughness, hydrophilic surface, surface conditioning, macro- and micro-geometric pattern and/or micro- and macro-morphological surface irregularities (as those previously referenced and described above) to promote and prevent specific cell populations from soft tissue attachment and/or adherence. An example of this concept would be a biologically active surface that will prevent the apical (downward) migration of sucular epithelium onto the entire surface of the hollow shell. A further example would be a biologically active surface that will prevent an apical migration of the Junctional Epithelium onto the surface of an immediate implant abutment that would otherwise be an area with dentogingival fiber attachment. In conclusion, the hollow shell with a biologically active surface is capable of controlling selective cellular repopulation along its surface thereby promoting a true re-attachment and/or adherence of the immediate soft-tissue extraction site.

The present invention also includes another important concept that the biologically active surface can also prevent undesirable cellular attachment and/or adhesion in addition to the general concept of preserving and promoting re-attachment.

As will be explained more fully in the following, the present invention allows this placement of the properly sized and shaped shell 10, in the soft-tissue socket, with complete freedom of motion in the x-, y- and z-directions and, just as importantly, with complete freedom of rotation about all three axes. This is done by mechanically de-coupling the abutment that is formed by this shell and the post 10, from the solid implant that must be rigidly fixed in the bony socket at its own optimum angle and depth.

A dental implant 30 having an implant axis 32 is provided and is adapted for placement in the bone socket immediate after tooth extraction, clearing and dressing of the bony socket in a conventional manner, for example, by removing debris and drilling an immediate implant receiving bore in the bone or bony socket using known techniques.

The temporary post 40 is then rigidly connected to and is coaxial with the dental implant 30, for example, by using a screw 50 that is inserted into a central bore in the post 40 and screwed into a treaded bore in the top center of the implant 30. A head 52 engages an annular step in the post 40 in a known manner, to fix the post 40 to the implant 30. The temporary post 40 extends in the interior volume of the hollow shell 10 but is not yet connected to the shell, and need not even touch the shell, so that despite the fixing of the post to the implant, the shell can be engages to the soft-tissue socket without directional or rotational limitation.

An initially fluid luting compound is filled into the interior volume between the shell 10 and the temporary post 40 and is allowed to set solid. Only then is the shell 10 fixed to the dental post 40 and implant 30, with no other previous connection between the shell and the implant so that the outer surface of the shell engages against the soft tissue socket without gaps and without requiring any alignment between the shell axis 12 and the implant axes 32.

As shown in FIG. 12, with shell 10 is seated in soft tissue socket 108 immediately after a tooth is extracted from and the shell seals the bone socket 106 in the jaw bone 112.

Figure 3:
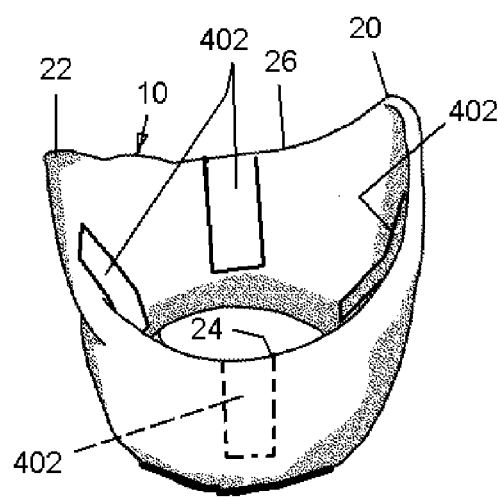
FIG. 3 is a perspective view of a still further embodiment of the shell of the invention for use in replacing a different tooth type and illustrating the interior markings for use as drilling guides according to the invention.

As illustrated in FIG. 2 the lingual valley 24 is lower than the facial valley 26 for mimicking maxillary and mandibular incisors for example. For mimicking maxillary and mandibular canines, the valleys 24 and 26 can be of substantially equal in height. For premolars and molars, the opposite of incisors is true so that as shown in FIG. 3 the lingual valley 26 is higher than the facial valley 24 and mesial and distal peeks 20 and 22 are not as highly scalloped as in incisors.

FIG. 2 also illustrates three different surface treatments for the three zones of the soft tissue socket.

Methods and Procedures of the Invention:

The method of the invention permits immediate implant soft-tissue abutment temporary placement at the time of tooth extraction to re-establish an effective biologic-seal of the soft-tissues to the surface of the abutment or shell more effectively to its anatomic shape.

The Immediate Implant Soft-tissue Abutment Temporary May be:

1. An immediate soft-tissue implant abutment temporary extending from the crest of bone 112 to the height of the remaining soft tissues 110. The immediate soft-tissue abutment temporary will re-establish a biologic-seal preserving the gingival soft tissues after the removal of a tooth and the immediate placement of an implant. It also enables containment of bone regenerative materials and primary coverage of the barrier membrane if used after tooth removal; and/or 2. An immediate tooth-form implant temporarily re-establishes a biologic-seal preserving the gingival soft tissues after the removal of a tooth and the immediate placement of an implant. It also enables containment of bone regenerative materials and primary coverage of the barrier membrane if used after tooth removal.

The immediate implant soft-tissue abutment temporary is a temporary component that connects to the implant-platform (superior surface of the implant platform) at the bone crest and extends to the level of the free-gingival margin of the soft tissue. It provides the necessary shape and adaptation to re-establish a biologic-seal between the soft-tissues and the surface of the temporary with a biologically active surface. The outer surface may be one or more different combinations of biologic agents, creating of a macro- and micro-geometric pattern and/or micro- and macro-morphology surface irregularities (as those previously referenced and described above).

The Immediate Implant Soft-tissue Abutment Temporary, i.e. Shell 10, Method has the Following Features or Steps:

1. The method and device in the preferred embodiment use a surgically sterile surface for shell 10 with a bi-layer micro-texture to promote immediate soft-tissue repair and adaptation promoting re-attachment or repair to the biologic surface. It is anticipated that the surface may have a regular micro-geometric pattern that is uniform. It is also anticipated that the surface texture may be modified chairside using a rotary instrument such as a uniquely designed dental bur, that results in a ordered microgeometric repetitive surface pattern in the form of alternating ridges and grooves, each having an unfixed width in a alternating range of about 2.0 to about 25 microns (micrometers) and a nonfixed or altering depth in a range of about 10 microns to about 50 microns, in which the microgeometric repetitive patterns define a guide soft-tissue preservation and re-attachment of soft tissue fibers to the surface of the immediate implant soft-tissue temporary abutment.

2. The shell is hollow and is of generally tubular design to accommodate the position of an immediate root-form implant 30 positioned at multiple locations within the residual socket.

3. The method and device provides an immediate mechanical seal between the residual soft tissue socket and the surface of the immediate implant soft-tissue temporary (Provisional) abutment.

4. The method and device promotes cellular soft-tissue attachment and/or adherence to the biologically active surface of the immediate implant soft-tissue temporary (Provisional) abutment.

5. The method and device retards cellular soft-tissue attachment and/or adherence to the biologically active surface of the immediate implant soft-tissue temporary (provisional) abutment.

6. The method and device preserves the soft-tissue architecture of the gingival surrounding the immediate implant soft-tissue temporary (Provisional) abutment.

7. The method and device enables bone regenerative materials to be retained in any gap left around the top of the implant 30, and protected during initial healing but the shell, in effect, sealing this area from the outer end of the soft and bony sockets.

Critical to the design is creating an effective biological socket-seal between the surface of the abutment-temporary (provisional) to adequately support and seal the residual soft tissue socket at the time of placement. The subgingival shape of the temporary shell promotes biological socket seal by providing either an over-contoured or under-contoured emergence profile to compensate for the position of the dental implant.

Additionally, the abutment-temporary design provides a single uniform material within the soft tissue zone of the residual soft tissue socket that prevents a micro- and macroscopic gap between dissimilar materials in the soft tissue gingival zone.

The abutment-temporary subgingival emergence profile provides an over-contoured or under-contoured shape that is anatomical to compensate for the three dimensional position of the underlying endosseous implant spatial position.

The abutment-temporary dental implant prosthesis is designed to be an interim prosthesis that is fabricated chair-side and is customized to provide individual unique tooth replacements. The temporary shell is designed from a series of elliptical and asymmetric shapes that have an eccentric opening for access to accept a cylindrical component that is attached via a screw mounting to the dental implant.

A self-curing material is used to affix the shell to a screw-retained temporary post 40 during the chairside fabrication of the abutment-temporary. The abutment-temporary (provisional) is modified chairside to generate a unique final shape and provide an adequate seal between the abutment-temporary (provisional) and the soft tissue socket. Preformed non-concentric elliptical shells provide a matrix to fabricate the abutment-temporary dental implant restoration.

The immediate abutment-temporary, that can also be thought of as an immediate provisional abutment, has one interface region between the dental implant and the overlying abutment-temporary. The interface is at the level of the implant buccal plate and contained at the level of bone crest. This eliminates the micro- and macroscopic gap from being positioned within the soft tissue zone of the soft tissue residual socket for immediate implant placement into a fresh extraction site.

Description of Methods:

It is understood in the description of the method and device that the placement of an immediate soft-tissue preservation implant abutment has the intended use for the extraction and replacement of a single tooth or multiple teeth. The method will describe for a single tooth, but it is understood that the deception of the method and device is note limited to a singular tooth but implies a description for multiple teeth as additional embodiments of the invention.

It is understood in the general description of the method of application of the device that the hollow shell will be placed at the time of the removal of a tooth and at immediate placement of a dental implant. It is understood that the hollow shell will serve as a temporary abutment for a period of time immediately following the removal of the tooth. The temporary abutment is placed immediately upon tooth removal and approximates the entire surface of the soft-tissue without gaps between the surface of the hollow shell and the connective tissue. This allows the gingival tissue to re-establish the adherence/attachment that was present prior to removal of the tooth thus preserving the contour of the papilla and gingiva. It is understood that this newly formed connection of the surface of that hollow shell and the connective tissue will be disrupted and disturbed upon the placement of the final implant abutment and implant crown prosthesis. This is not of critical consequence as the long as the subsequent prosthesis is placed immediately after removal. It has been found that a minimally invasive technique followed by immediate placement of either the temporary abutment and/or final implant abutment results in a minimal disruption to the tissues. It is conceived that the final implant abutment prosthesis will have the same shape, contour and texture as the temporary abutment that was used. This will then allow the soft-tissue zone to re-establish to the newly placed final implant abutment and restoration. The placement of the final implant abutment will be inserted immediately upon the removal of the temporary abutment to ensure that tissue changes and remolding does not occur. It is conceivable that a temporary implant abutment is fabricated via a CAD/CAM technology so that it will become the final prosthesis and not require removal after placement. It is conceivable that the CAD/CAM temporary abutment will possess all of the contour, shape and textures previously described.

It is understood that the immediate placement of both the temporary and final prosthesis is critical to prevent the soft-tissue zone from healing with scare formation and/or remolding of the connective tissues. Immediate placement of both the temporary and final implant abutment with a minimal invasive technique herein described preserves the soft-tissue zones of the sulcular epithelium, junctional epithelium and dento-gingival fibers. It is contra-indicated to use a delayed approach for either the temporary or final abutment prosthesis as this will promote wound healing that has been shown to result in epithelum covering the entire wound with a remoldening of the tissues losing the peak to valley natural contour. A delayed approach often results in scaring and adaption of the soft tissues and a re-arrangement of the three zones which have been detailed within this description. Therefore, the placement of both the temporary and final prosthesis immediately after the removal of either the tooth or temporary implant abutment is critical to the health and preservation of the soft-tissue zone. The temporary element to immediate implant is another factor which distinguishes this method with all other previously described methods and techniques. The structural configuration of three zones within the soft-tissue zone upon the hollow shell following a peak and valley configuration is also important to the maintenance and re-establishment of a biologic and functional attachment of the supra-crestal soft-tissue zone.

The diagnosis that a tooth requires extraction is determined by the dental clinician. The diagnosis is preformed using conventional means including clinical examination, radiographic analysis, detailed past dental history and the review of signs and symptoms. The patient is informed of the treatment alternatives and an appropriate informed consent to treatment is provided to the clinician.

Prior to the extraction of the tooth a clinical photo can be taken to allow future comparison of the pre-treatment condition that was present versus the post-operative outcome after treatment is completed. The photo may have a reference measurement tool or instrument so that detailed analysis of the soft-tissue changes can be analyzed.

A Dental impression either using conventional impression materials such as alginate, polyether, vinyl polysiloxane, and other materials to establish an accurate representation of the teeth and surrounding gingival tissues. It is understood that the described embodiment may also be performed using a digital impression such as cone beam computer tomography or digital oral impression (CAD/CAM Digital Impressions) using a hand-held oral scanning device of known design.

The area of the mouth in which the tooth is to be extracted is anesthetized with a dental local anesthetic solution. A local anesthetic solution is can be delivered to the area either as local infiltration dental injection or as a regional nerve block to the area. The patient is given adequate time (typically 5 minutes) for the dental local anesthetic to anesthetize the region of the mouth that is being treated.

Extreme care is used to preserve the entire tissue-zone and minimize trauma to the supporting gingival tissues during each phase of treatment. It is critical to preserve the soft-tissue architecture of the immediate and surrounding gingival in order to re-establish the biologic-seal after the tooth is removed and the immediate soft-tissue implant abutment, i.e. shell 10, is placed. Therefore a flapless surgical technique is used.

The first step to performing this method is to carefully incise the entire supra-crestal attachment of the tooth 360 degrees around the tooth, i.e. around soft tissue socket. It is important to surgically disconnect the soft-tissue attachment fibers. This can be accomplished using a surgical blade, piezo-surgical instrument, micro-rotary dental handpiece or dental laser soft-tissue cutting instrument. The method requires careful dissection of the supra-crestal attachment which includes the sucular epithelium, junctional epithelium, connective tissue inserting fibers which are found between the connective tissue and the surface of the root above the crest of bone. Once the supra-crestal fibers are released the superior periodontal ligament fibers (attachment fibers found between the alveolar bone socket and root surface) can next be incised.

The superior periodontal fibers attach the surface of the tooth (cementum) to the inner bony socket must also be severed using minimal disruption to the surrounding soft-tissue and bony architecture. This can be accomplished by using micro-surgical instruments, periotomes, a rotary diamond pointed diamond, piezeo-surgical instrument, laser. It is important that the instrument diameter is between approximately 20 microns to 50 microns (or ⅛ to ¼ millimeter in diameter) as this is the dimension of the width of the periodontal ligament space. The surgical instrument is placed into the entrance of the periodontal ligament between the tooth and inner socket wall. The periodontal attachment fibers are served around the tooth to a depth of 1 to 4 mm, depending on ease of entry into the periodontal ligament space.

The extraction of the tooth is first initiated using a rotational movement in order to sever the remaining sub-crestal periodontal fibers attaching the tooth to the inner socket wall. This can be performed with either using a reduced diameter elevator, periotome or extraction forceps. Once a rotational movement is achieved a vertical force can be applied to the tooth to advance the root out of the bony socket.

When the extraction is performed using this method minimal disruption can occur to the surrounding soft-tissues of the gingival. The interdental papillae are not surgically altered from the pre-treatment condition. Incisors are not made which compromise the blood supply to the region of the bone or surrounding soft-tissue gingival. The architecture of the soft-tissue has not be altered other than the severing of the attachment fibers between the root surface and inserting fibers.

Removal of any inflammatory granulation tissue within the bony socket may be necessary. This is performed using a small sized circular curette. Inspection is performed to ensure the integrity of the remaining inner socket walls. A radiograph may be taken to determine the remaining configuration of the tooth socket. This step is referred to here as preparing the bony or bone socket.

Immediate insertion of dental implant 30 is performed. A dental implant is immediately placed within the residual extraction socket. The term "immediately" as used here means that the implant is placed shortly after the bony socket has been fully prepared to receive the implant, 10 to 30 minutes for example, but importantly during the same patient's visit.

The vertical position of the implant: The implant 30 can be placed at the level of the remaining crest of bone. Since the remaining crest of bone has different heights the implant may be slightly supra-crestal as one region and slightly subcrestal at another region of the socket, this is to be expected.

The horizontal position of the implant: The implant is to be ideally placed with the axial position allowing for a screw-retained temporary. The center axis of the implant must therefore be placed in the position of the cingulum of the adjacent teeth; i.e., positioning the implant toward the palatal (lingual) aspect of the residual extraction socket. It is noted that the implant 30 will not be placed in the center of the socket 102 as this would result in the retention screw of the immediate-temporary to exit through the incisal edge of the tooth and will result in an esthetic compromise of the restoration. Positioning the implant biased toward the palatal (lingual) position of the extraction socket is critical so that a screw-retained immediate temporary restoration can be used. This advantageous placement of the implant is made possible by the fact that the abutment or shell 10 of the invention is mechanically de-coupled from the implant and need not be affixed with respect to the axis or position of the implant as has been common in the past. The preferred embodiment of the invention is an immediate screw-retained temporary to eliminate the need for cementation of the temporary. Retention of the immediate temporary relies upon mechanical retention of the screw. It is anticipated that the immediate temporary could be designed in with a temporary design in which it is cemented to the substructure directly and places the location of the micro gap below the soft tissue zone.

The immediate implant 30 must mechanically engage and lock into a portion of the remaining bone. This may be achieved at the apical end of the implant. It may also be achieved on a lateral portion of the surface of the implant.

It is understood that the implant diameter will be smaller then the greatest diameter of the root of the tooth that was removed. Therefore the dissimilar diameters between the immediate implant and the residual bony tooth socket must result in a "gap" or space between the residual bony socket and the surface of the implant 30. Filling the entire tooth socket is not desirable, as this method relies upon a residual gap between the facial surface of the immediate implant and the remaining buccal plate of bone. This gap will then allow for the placement of a bone regenerative material to be placed between the implant surface and the inner tooth socket buccal plate. The gap allows for future bone regeneration via the in growth of the blood supply and new osteoblasts. It is important not to use a implant diameter that would make direct contact to the labial plate of bone as this would compromise the blood supply that is needed to preserve the labial (buccal) plate of bone as the implant surface provide no ability for angiogenesis. This is critical point to appreciate and understand. The preservation of the overlying gingival and surrounding soft-tissues is preserved by several critical factors: (1) a minimally invasive surgical approach; (2) preservation soft-tissue architecture; and (3) preservation and promotion to re-establish the blood supply to the surrounding tissues.

Placement of the immediate soft-tissue implant preservation abutment shell with a biologically active surface involves a screw-retained temporary post 40, such as the PreFormance Post from Biomet 3i Dental Implants of Palm Beach Gardens, Fla., is connected to the dental implant 30 held within the bone. The immediate soft-tissue abutment shell 10 is selected for the proper vertical and horizontal dimensions. The immediate soft-tissue preservation abutment shell 10, as noted above, is supplied in different dimensions depending upon the tooth to be replaced. It will have series of defined dimensions externally. These dimensions will include a series of different tissue-zone heights ranging from 2 mm to 5 mm. It will be provided in several root form configurations and be provided in more then one horizontal widths. An example of the horizontal dimensions could be, but not limited to:

Maxillary Right Central Incisor:
Height 2 mm, Height 3 mm, thru 5 mm.
Diameter, Small, Medium and Large.
An irregular superior surface is provided to conform to the soft-tissue gingival architecture. The interproximal points will be longer in dimensions then the labial and lingual surfaces.
The inner shell allows for the eccentric position of the shell over the center axis of the implant held within the bone.

Maxillary Right Lateral Central Incisor:
Height 2 mm, Height 3 mm, thru 5 mm.
Diameter, Small, Medium and Large.
An irregular superior surface is provided to conform to the soft-tissue gingival architecture. The interproximal points will be longer in dimensions then the labial and lingual surfaces.
The inner shell allows for the eccentric position of the shell over the center axis of the implant held within the bone Maxillary Right Canine:
Height 2 mm, Height 3 mm, thru 5 mm.
Diameter, Small, Medium and Large.
An irregular superior surface is provided to conform to the soft-tissue gingival architecture. The interproximal points will be longer in dimensions then the labial and lingual surfaces.
The inner shell allows for the eccentric position of the shell over the center axis of the implant held within the bone.

Maxillary Left Central Incisor:
Height 2 mm, Height 3 mm, thru 5 mm.
Diameter, Small, Medium and Large.
An irregular superior surface is provided to conform to the soft-tissue gingival architecture. The interproximal points will be longer in dimensions then the labial and lingual surfaces.
The inner shell allows for the eccentric position of the shell over the center axis of the implant held within the bone.

Maxillary Left Lateral Central Incisor:
Height 2 mm, Height 3 mm, thru 5 mm.
Diameter, Small, Medium and Large.
An irregular superior surface is provided to conform to the soft-tissue gingival architecture. The interproximal points will be longer in dimensions then the labial and lingual surfaces.
The inner shell allows for the eccentric position of the shell over the center axis of the implant held within the bone.

Maxillary Left Canine:
Height 2 mm, Height 3 mm, thru 5 mm.
Diameter, Small, Medium and Large.
An irregular superior surface is provided to conform to the soft-tissue gingival architecture. The interproximal points will be longer in dimensions then the labial and lingual surfaces.
The inner shell allows for the eccentric position of the shell over the center axis of the implant held within the bone.

It is understood that each shells 10 can be for the specific tooth being replaced. The dimensions of the shell are based on measurements of numerous soft-tissue sockets remaining after tooth removal. The shell 10 has the requirement to enable a soft-tissue socket-seal to be re-established. This is predicated upon allowing the proper dimensions to completely fill the soft-tissue (tissue-zone) socket.

In general terms and from observation of stone casts and extracted teeth as well as descriptions, pictures and illustrations in Dental Anatomy book, it seems that the "lingual valleys" are lower than "facial valleys" in maxillary and mandibular incisors. Max. and mand. canines "valleys" are of about equal height. Max. and mand. premolars and molars seem the opposite of incisors where "lingual valleys" are higher than "facial valleys" and mesial and distal peeks are not as highly scalloped as in incisors. Of course there are always exceptions and slight variations to the rule since each person dental anatomy will vary.

The preferred embodiment of the immediate soft-tissue implant preservation abutment shell is generally defined as a "tubular shell" which is open at both ends at perimeters 16 and 18. The inferior is placed into the soft-tissue socket to make direct contact with the implant head platform of the implant 30 within bone 112. The superior surface is to approximate the free-gingival margin of the surrounding tissue-zone. The outer surface of the shell 10 is to make direct contact with the inner soft-tissue residual socket. The outer surface composed of a bioactive surface that is defined by but not limited to, a particular surface texture, surface roughness, hydrophilic surface, surface conditioning by applying bio-active agents, creating of a macro- and micro-geometric pattern and/or micro- and macro-morphological surface irregularities (as those previously referenced and described above) to promote soft tissue attachment and/or adhesion of the dentogingival complex.

It is anticipate that this biologically active surface may also retard the growth of pathogens and/or specific cell types during healing of the soft-tissue socket. It is also conceivable that the biologically active surface will control and regulate selective cell repopulation along the surface of the hollow shell from the application of the biologic agent to said surface. The final adapted shell eliminates all openings and gaps between the soft-tissue socket and surrounding gingival. This re-establishes a biologic-seal to the underlying tissues below the surface. This will also provide containment and protection of any bone regenerative materials that are placed between the surface of the bone socket and the surface of the implant filling the "gap" between the dissimilar diameters of these two structures. If necessary a membrane can be placed at the level of the bony crest and placement of the shell 10 will provide complete coverage of the membrane below providing a biologic-seal to the outer oral environment. Once the shell is filled (see step 10 below) and modified it will also provide structural support to the soft-tissue gingival to prevent and preserve the architecture. The surface of the immediate abutment shell promotes soft-tissue adhesion to the surface. Allowing the superficial layers of the dermis to adhere to a smooth superior region of the abutment shell as well as encouraging functional fiber orientation to the roughened inferior region to promote a functional connective tissue attachment.

Luting (chair-side connection) of the immediate soft-tissue implant preservation abutment shell to the retaining screw-post of the implant: Once the proper abutment shell is selected from the variety of sizes and diameters it is placed within the tissue-zone soft-tissue socket. It is eccentrically positioned to the implant as previously described so that the outer surface of the shell make physical contact ensuring a biologic-seal between soft-tissue and surface of the shell. It is luted or connected to the screw-post in this position by using a chairside technique. The technique of connecting the shell 10 to the screw-post 40 can be performed with a variety of materials in the preferred embodiment a cold-cure acrylic is used, in additional embodiments any number of polymerization materials can be used but not limited to composite, acrylic, resin, etc. The entire internal surface of the shell 10 is filled with luting compound and eliminating voids or gaps within the material.

The superior surface can be filled to the level of the free gingival margin. An access hole will remain to allow removal of the shell, e.g. but inserting a nylon plug into the central hole of the post 40 for final finishing and temporary insertion.

The inferior surface is modified and any gap or voids are filled chair-side and then re-surfaced as described below.

Re-surfacing of the shell material, preparation and handling: In certain situations it may be necessary to modify the shape and surface of the shell 10 to properly adapt to the soft tissue socket. An additive technique of material or subtractive technique can be required in which additional materials or added or removed. To resurface the modified outer shell a novel surface texture bur is attached to a standard rotary handpiece. This preservation abutment shell bur is designed to re-establish the surface texture that was created in the texture zone on the outer surface of the abutment shell. It is conceivable that the application of the biological agent will be applied at the time of placement of the hollow shell into the extraction socket. This includes but not limited to a chairside application of a specific biologically active agent upon the outer surface of the hollow shell. A second (or third) step of cleaning may then require removal of all contaminants. This surface cleaning step is accomplished by thorough cleaning, in the preferred embodiment this can require high-pressure, high-heat steam cleaning in alternative embodiments it is anticipated that autoclave, antimicrobial cleaning solutions may be applied to the surface to detoxify the contaminated surface.

After filling and reshaping of the shell 10 is completed it is removed from the implant by un-screwing the retaining screw 50. The abutment shell is then cleaned and inspected and all voids are filled and re-surfaced and cleaned as described above.

Placement of a standard cylindrical healing abutment is attached to the plate-form. The standard cylindrical healing abutment may be composed of titanium, stainless steel, anodized metal or other metal. It is conceivable that the standard cylindrical healing abutment is made from a cost saving polymer and disposed of after removal as this component is to be used as an intra-operative space maintaining during the placement of bone regenerative materials during this method. The standard healing abutment is selected to attach to the implant resulting with a noticeable gap between the outer surface of the standard cylindrical healing abutment and the soft-tissue socket. Bone grafting materials are placed within the gap between the bony socket and surface of the implant 30 at or below the crest of bone. An optional barrier membrane can be positioned if necessary before or after the bone grafting materials being put into placed.

The standard cylindrical healing abutment is removed and discarded and the contoured refinished abutment inserted. In the preferred embodiment the retaining screw is put into placed and applying a seating torque to the screw that is between 15 newton-centimeters to 35 newton-centimeters.

The abutment shell 10 is adjusted to ensure that it is not in occlusal contact with the opposing teeth when the patient closes their mouth.

A final radiograph is taken to assess the fit and position of the implant and shell.

The abutment shell 10 creates a biologic-seal to the underlying soft tissue and preserves the integrity of the surrounding gingival architecture. The abutment shell 10 is not to be removed for a minimum of 3-4 months at which time the fabrication of the final prosthesis can be initiated.

Further Structural Details of the Invention:

As noted, illustrated and described above, abutment shell 10 in its preferred form, is generally a tubular shell which is open at both ends. The tubular shell has the following specifications but it is anticipated that it may also have other designs features:

The shell is an irregular tubular design that mimics the shape of residual soft-tissue (tissue-zone) socket that remains after a tooth has been removed. Examples of these shapes (generally occlusal views) are provided in FIGS. 2-5. The shape may more closely mimic the cross-sectional outline of a root in the tissue-zone region, but may also be designed to over-compensate on one or more surfaces to ensure physical contact along all aspects of the soft-tissue tooth socket. It is critical that the shell's fit with contact and not be causes excessive contact pressure at any specific point or area of the soft-tissue socket.

Outline shape of the two ends of the preservation abutment shell 10 is irregular as also illustrated in the drawings. The superior (gingival) surface of the shell (at outer perimeter 18) has a larger area when compared to the inferior (implant) surface (at inner perimeter 16) that comes into contact with the platform head of the implant 30.

The vertical height of the tubular shell will not be uniform. The interproximal surfaces at peaks 20 and 22 have a greater height when compared to the buccal and lingual surfaces at 24 and 26 of the tubular shell 10.

The emergence profile of the shell is one that has a variety of profiles to compensate for the position of the implant within the residual socket. Since the implant is to be intentionally placed off-center from the extracted tooth, the shell is intentionally placed eccentric to the immediate implant 30, placed within the bone. The shell is designed to be placed eccentric to the implant head. The emergence profile of the shell is over-compensated and under-compensated in the profile design allowing for the position of the implant. The compensating emergence profile design and ability to place the shell eccentric enables the re-establishment of an effective biologic-seal between the outer surface of the shell and the residual soft-tissue perimeter. The shell can be confined to the transmucosal (tissue-zone) region extending from the crest of bone to the free gingival margin or it may continue to extend into the oral cavity as the labial surface of material to replace the labial surface of the removed tooth in addition to the transmucosal region.

Surface Texture and morphology of Shell—In the preferred embodiment the outer surface text design can possess three distinct surface texture zones or bands which follow the contour of the peaks and valleys of the upper (coronal) edge of the hollow shell (FIG. 2). These three different bands are distinct from one another and run parallel to the coronal edge of the hollow shell and to one another, FIG. 2 at zones 302, 304 and 306. The upper (coronal) band of the hollow shell can be smooth to discourage the accumulation of plaque, 302. The smooth band extends 1 mm to 3 mm vertically and corresponds to a region found on a tooth as depicted in FIG. 11, 202. This region on a tooth is a scalloped, circumference band (302) of the tooth in contact with the sulcular epithelium. It is preferable that the surface be smooth to minimize the accumulation of plaque and bacteria as seen in FIG. 2 at 302. After placement and healing of 10 into the mouth of a patient, the smooth surface of 302 approximates the sulcular epithelium of the gum, FIG. 12 at 302, and can be effectively cleaned and maintained in a state of health as this surface can is easily cleaned do to the smooth surface.

The middle band of shell, FIG. 2 at 304 is the zone of the hollow shell that approximates the junctional epitheialium corresponding to the region on the tooth, FIG. 11 at 204. This band extends 0.25 mm to 1.35 mm vertically. The middle band of the hollow shell is textured with vertical and oblique grooves, FIG. 2 at 304 and forms a circumferential band around the hollow shell as do all three bands herein described. This middle band follows the peak to valley configuration of the two other zones described. The grooves are separated by a distance between 5-7 microns and are a depth of 10-20 microns. This textured zone is 0.25 to 1.35 mm in height possesses an ordered microgeometric repetitive surface pattern. This band corresponds to the region on the tooth, FIG. 11 at 204 in which the Junctional Epithelium of the gum attaches to the tooth via the hemidesmosome attachment. After placement and healing of 10 into the mouth of a patient, the vertical and oblique grooves of surface of 304 approximates the junctional epithelium of the gum, FIG. 12 at 304, and provides a surface to which the soft tissue can establish adherence of the junctional epithelium to the surface of the shell to create a functional barrier and seal resulting in a state of health.

The inferior (apical) textured band of the hollow shell (FIG. 2, 306) covers the remaining outer surface. This textured surface encourages the re-establishment of the gingival fibers to make contact and adhere to the surface of the temporary abutment. This band of the hollow shell is textured with a pitted-roughened surface (FIG. 2, 306) with a diameter of 25 to 50 microns and 5 to 10 microns in depth for the surface texture. This band measuring 1 mm to 3 mm in vertical height. This apical band follows the peak and valley contour of the other two bands on the coronal aspect, while the inferior aspect follows the contour of the apical edge of the hollow shell, FIG. 2. The surface of the inferior band of the hollow shell approximates the dento-gingival fibers seen in FIG. 12 at 306, this corresponds to the region of the tooth that is attaches to the dento-gingival fibers of the tooth, FIG. 11 at 206. After placement and healing of 10 into the mouth of a patient, the micro-pitting and roughened surface enables the dentogingival fibers to insert directly into the surface of the shell producing a stable functional gingival attachment to this region of the hollow shell, FIG. 12 at 306. It is conceivable that this band of the hollow shell is coated with a biologically active agent that produces proteoglycans and cementogenesis to further encourage the dento-gingival fibers to insert into the surface.

The surface texture is not limited to two or more texture patterns, it is conceivable that the surface of the shell be design with a single texture covering the entire surface or designed from multiple textures to encourage direct soft-tissue adaptation within the tissue-zone. A smooth surface at the superior regions discourages plaque accumulation while the textured surface promotes and accelerates effective soft-tissue adhesion. The surface design discussed in the preferred embodiment has been shown to promote soft-tissue preservation in combination with providing an effective biologic-seal of the surface of the shell to the residual soft tissues. A bioactive surface that is defined by but not limited to, a particular surface texture, surface roughness, hydrophilic surface, surface conditioning by applying bio-active agents, creating of a macro- and micro-geometric pattern and/or micro- and macro-morphological surface irregularities (as those previously referenced and described above) to promote soft tissue attachment and/or adhesion of the dentogingival complex.

Material—the shell can be composed of a variety of biocompatible materials including but not limited to; ceramic, acrylic, porcelain, lithium disilicate, zirconia and other crystalline structure. It is anticipated that this material can be composed of materials that are anti-microbial, bacteriostatic to retard the growth or colonization of the surface and internal surfaces with micro-organisms. Examples of such materials include but are not limited to; silver, copper, magnesium, titanium, hydroxyapitite, etc. These materials can be incorporated into the shell material or may be applied to the shell surface forming a second layer.

The connection interface of the abutment shell is placed at the level the implant head platform. In the preferred embodiment there is a single interface at the implant plateform at the bone crest level. This interface is a mechanical connection to minimize the placement of a micro- or macro-connection gap within the tissue-zone. The preferred embodiment is screw-retained. It is anticipated that a cementable version of the immediate soft-tissue implant preservation abutment shell can be fabricated.

The preferred embodiment of the shell is confined to the tissue-zone, but it is anticipated that a second design could include part of all of the tooth form that was extracted.

A tooth-form temporary (not shown) that is selected or created to match the extracted tooth, is then luted to the outer perimeter 18 of shell 10 so that the patient leaves with a cosmetically equivalent tooth replacement to the one extracted.

Disposable Standard Cylindrical Implant Intra-operative Abutment:

This component is used as intra-operative abutment that is placed during the immediate soft-tissue implant preservation protocol to allowing bone grating materials to be placed within the bone gap between the implant surface and the bony residual socket. It also has the function to prevent bone grafting materials from entering into the internal screw hole of the implant prior to the placement of the immediate soft-tissue implant preservation abutment. It is a single use, disposable component. It can be fabricated from a variety of materials and come in a variety of heights and widths. The preferred embodiment is an inexpensive polymer material allowing it to be screwed or press-fitted into place during the placement of the bone grafting materials.

Immediate Soft-tissue Abutment Texturing Bur:

This component is a rotary bur that is designed to provide a microgeometric repetitive surface pattern forming a varying widths and varying depths ranging from 10 microns to about 50 microns. The irregular repetitive pattern is created using a chair-side rotary instrument on the surface of the immediate soft-tissue implant preservation abutment to resurface the outer shell.

Immediate Soft-tissue Abutment Application of a Biologic Agent Upon the Outer Surface of the Hollow Shell:

The application may be applied chairside and at the time of tooth removal. It is conceivable that the biologic active surface is incorporated into the outer surface of the hollow shell and/or applied to the outer surface prior to the time of tooth removal. The surface may be composed of one or more biologic agents.

Improvements Over Prior Art:

Following are some improvements of the invention over known implant apparatuses and methods:

Preservation of the soft tissue architecture after the immediate removal of a tooth.

Support of the soft tissues to prevent collapse of bone and soft tissue during healing.

Creation a soft tissue "seal" of the replacement temporary to the overlying soft tissues. A soft tissue seal of the residual soft-tissue socket of an extracted tooth in which an immediate implant has been placed.

Produce soft tissue adhesion by providing direct physically contact between the prosthesis and surrounding soft tissue socket.

Placement of a single interface between implant and prosthesis that is below the soft tissue proximal heights at or below the level of supporting bone.

One-piece prosthetic design that is a temporary that is screw retained.

Prosthesis emergence profile is over-contoured to provide an adequate soft-tissue seal and soft-tissue support to the soft tissues to preserve the natural architecture of the gingival tissues.

Prosthesis is under-contoured to provide an adequate soft tissue seal between prosthesis and soft tissue socket to support the soft tissues to preserve the natural architecture of the gingival tissues.

The supra-gingival contour of the tooth prosthesis is identical to the natural tooth while the sub-gingival possesses a emergence profile contour that is either over-contoured or under-contoured to compensate for the lack of ideal position of an implant in the vertical, horizontal, and buccal-lingual, mesial-distal angulations.

Anti-rotational Prosthesis Screw-retained Temporary Prosthesis.

Anti-rotational Features in the Implant/Abutment Connection.

The temporary abutment is constructed directly chair-side utilizing a prefabricated series of anatomic shells who's central access is eccentric to allow either an over-contoured or under-contoured subgingival emergence profile thereby allowing adequate support of the soft tissue and ensuring a seal being formed between the soft tissue socket and the temporary prosthesis.

The temporary abutment is anticipated to prefabricate in a variety of sizes and elliptical shapes of the root surfaces. Different vertical heights will be provided. The shapes will be designed to represent replacement of an extracted tooth.

Antimicrobial Surface and/or Material to be Used.

Incorporation of a microtexture on the surface of the temporary that has a regular geometric configuration to encourage soft-tissue connection.

Use of a specialized bur that creates a regular pattern on the surface of the temporary.

The Following Designs are Anticipated, but not Limited to:

Temporary transmucosal (root form) implant temporary shell root form in the soft-tissue zone from the platform head of the implant to the free-gingival margin.

The superior 1-3 mm may be smooth surfaced to provide a plaque free zone.

Inferior surface (below the 1-3 mm plaque zone) may be textured to encourage soft tissue adhesion.

Surface Treatment of the Shell by Steam Cleaning

The transmucosal temporary component of the invention makes the physical and structural connection between the dental implant and the overlying soft-tissues for the final connection to a tooth replacement prosthesis visible inside the mouth.

The implant 30 and screw 50 are made of surgical steel or other metals such as titanium/titanium alloy. The post is made of steel, ceramic of other durable material such as gold alloy, e.g. AuPdAg (gold-palladium-silver). The shell is zirconium oxide ceramic or other suitable material as listed above. The luting compound is, for example resin or resin-ionomer. The tooth-form temporary 70 is made of material such as polymethyl methacrylate (PMMA), polyetheretherketone (PEEK), lithium disilicate, or zirconium dioxide.

Drilling Guide Feature:

A further and more general object of the invention is to provide a dental implant method and arrangement that uses a hollow shell 10 as shown in FIGS. 3-10, 13 and 14 with visual orientation guide markings 402 or physical orientation guide structures 502 and 602 to inform the operator of the spatial relationship of the residual soft-tissue gingival socket to the use of bone drilling burs and instruments. Thus the hollow shell 10 with peaks and valleys provides a spatial relationship during bone drilling and implant insertion phase after tooth extraction and during the immediate dental implant placement to the underlying bone. The shell is imbued with distinct visual and radiographic guide markers upon the hollow shell as illustrated in FIGS. 3 through 10.

Figure 4:
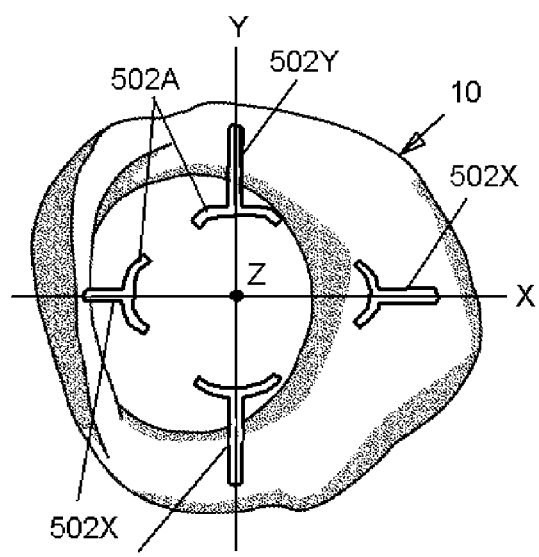
FIG. 4 is a perspective view of an embodiment of the shell of the invention that illustrated the asymmetry of the outer perimeter of the shell and also illustrating orientation directional guide posts to also aide in drilling according to the invention.
Figure 5:
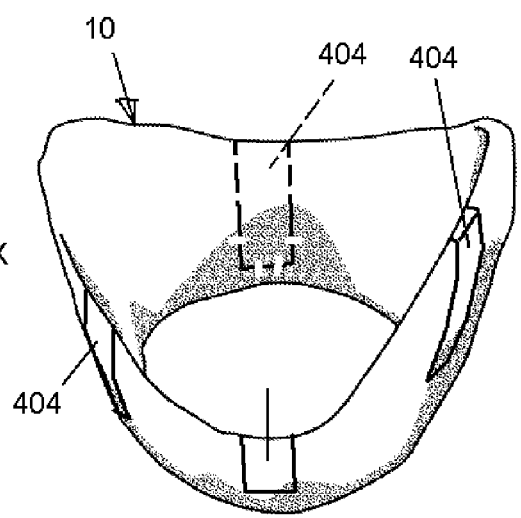
FIG. 5 is a perspective view of the shell of the invention shown also in FIG. 1 for comparison and illustrating external drilling guide marking of the invention.

These markings may be surface marking of a design of visual markings 402 on the inner surface of the 10 as shown in FIG. 3 or at 404 on the outer surface as shown in FIG. 5, or can be on the inner and/or outer surface of the hollow shell as shown at FIGS. 7 to 10. The visual guide markings provide an x-axis and y-axis of the horizontal plan as depicted in FIGS. 4 and 13 at marking posts 502X and 502Y and include curved marking arcs 502A, and in FIGS. 6 and 14 at marker posts 602Z that extend from the shell 10 in generally the Z direction that is substantially parallel to the implant axis 32 (FIG. 1) and with curved marker arcs 602A to help further visually guide the drilling direction of a dental drilling bur 804 in FIGS. 13 and 14, of a dental drill or handpiece 802.

Figure 8:
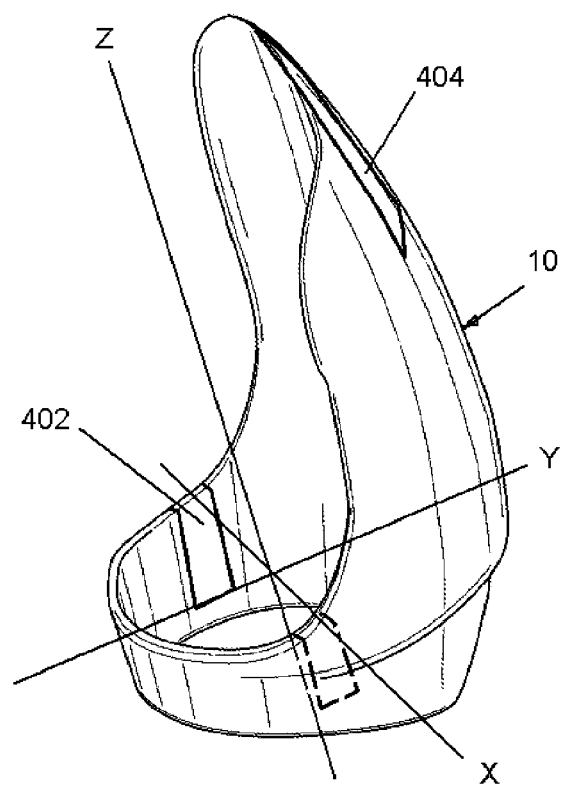
FIG. 8 is different perspective view of a shell like that of FIG. 7 but with inner markings.
Figure 13:
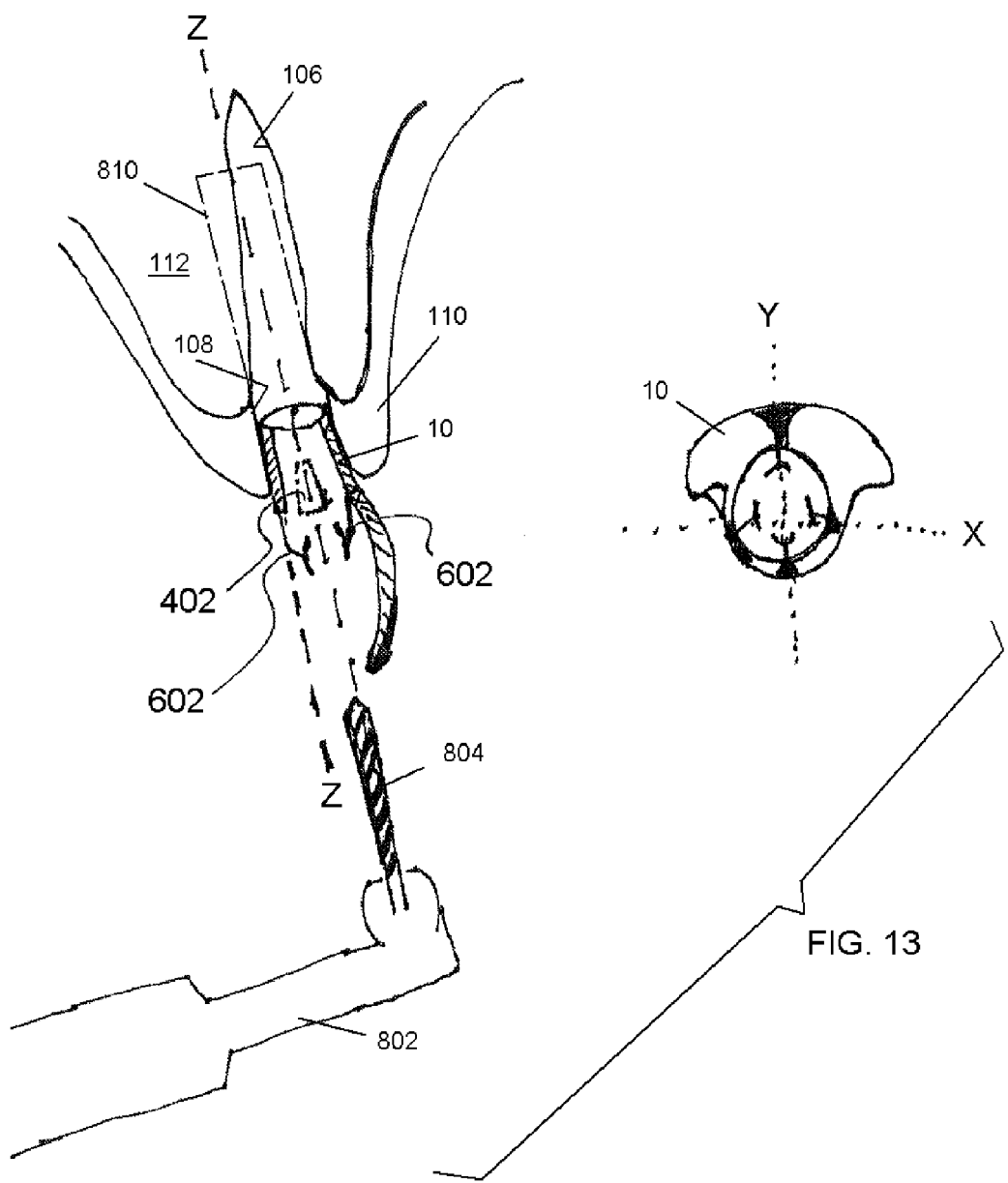
FIG. 13 is a composite view of an extraction site with one type of shell of the invention for use as a drilling guide for an implant hole at the site.
Figure 14:
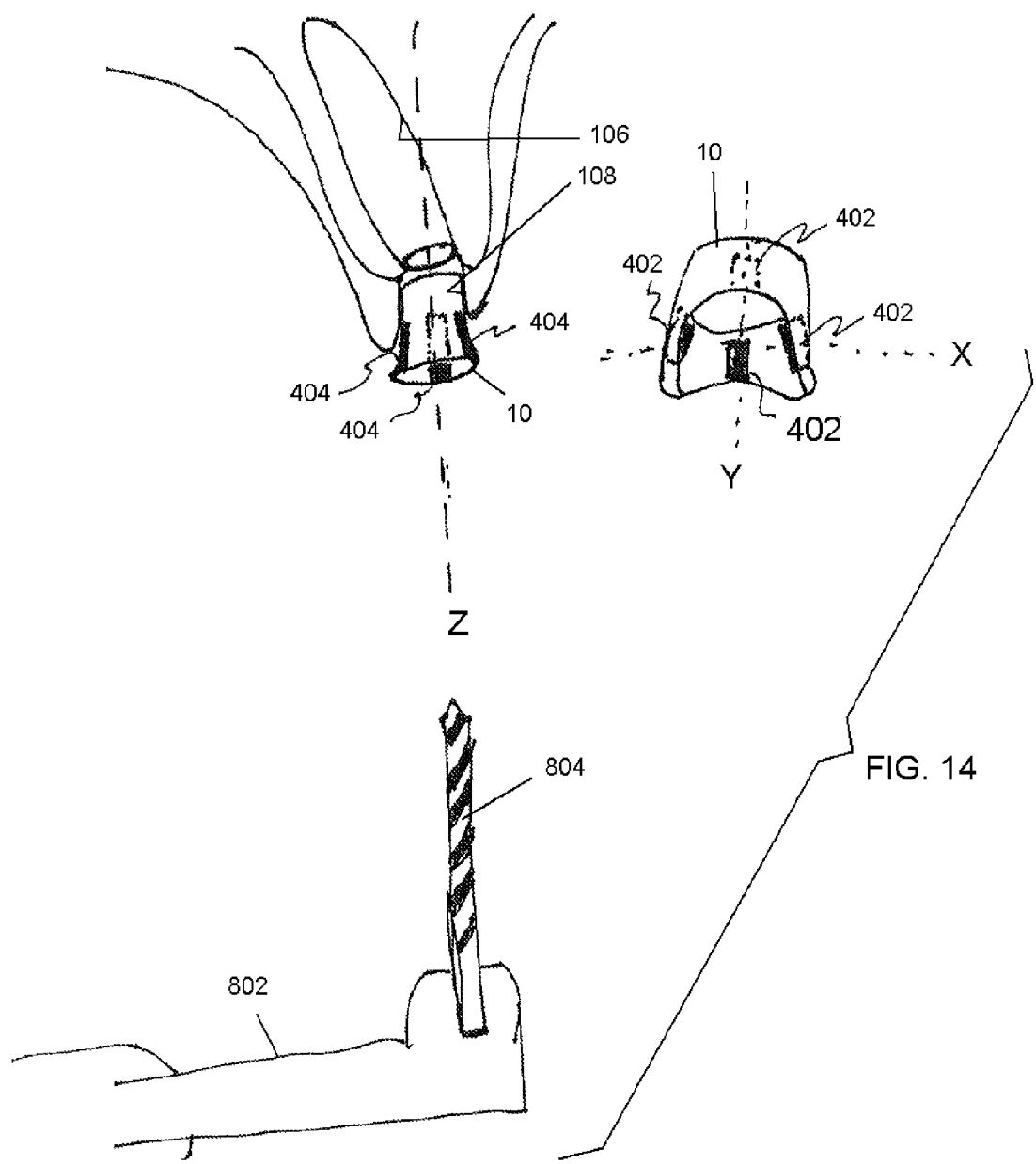
FIG. 14 is a view similar to FIG. 13 of another type of shell of the invention for use as a drilling guide for an implant hole at the extraction site.

The intersection point of these axes x, y and z provides a visual point at which the bone drill bur 804 can be positioned as best illustrated in FIGS. 13 and 14. The vertical long axis z of the visual guiding marking on the hollow shell, for example 402 in FIG. 8, provides the long axis of the vertical plan, providing the z-axis. The intersection of the three planes of space thereby providing a visual point of position of the bone drilling bur as well as the path that the drill bit should take as it drills into the underlying bone, depicted in FIGS. 13 and 14.

The physical markings may be visual guide markings such as laser etching, decals, colored markings and/or physical structural guides on the surface such as indents, detents, internal or external tabs. The preferred embodiment may be a combination of visual guide markings and/or winged-vertical-posts 502 and 602 providing a means of displaying spatial orientation of the hollow shell and its relationship to the residual soft-tissue gingival socket and underlying alveolar as in FIGS. 13 and 14. The preferred embodiment of these visual markings would be four separate vertical bars 402 or 404 that would are used to provide directional instruction and/or information to the position of the underlying bone. The orientation markings provide a visual instruction to the direction that should be used during drilling and insertion.

In another embodiment the outer and/or vertical inner markings on the surface of the hollow shell would correspond to the peaks and valleys of the design and mimic the shape and contour of the residual soft-tissue socket allowing the hollow shell to be provide an orientation to insertion of drilling instruments within the natural occurring peaks and valleys of the residual soft-tissue socket opening of the extracted tooth. These visual and/or physical markings simplify the insertion during the drilling and implant bone preparation phase of treatment by providing the horizontal x-axis, y-axis and z-axis to the residual soft-tissue gingival socket. The drilling bur is kept within the circumference of the hollow shell thereby relating the positioning the bone drill within the residual soft tissue socket in the horizontal plane and providing the vertical path that is to be taken when inserting the bone drill bur, all references from the residual soft-tissue socket. This technique would ensure that the final access hole to the implant prosthesis would be within the residual soft tissue socket circumference and angulated to exit within the confines of socket as well. The hollow shell provides prosthetic and surgical guide attributes and could be distinct and separate from the previous hollow shell with biologic surface characteristics previously described or it may be in combination with the a biologic surface as described herein. A variety of hollow shells are available with different lengths, widths, shapes and diameters in three dimensions of space.

Figure 6:
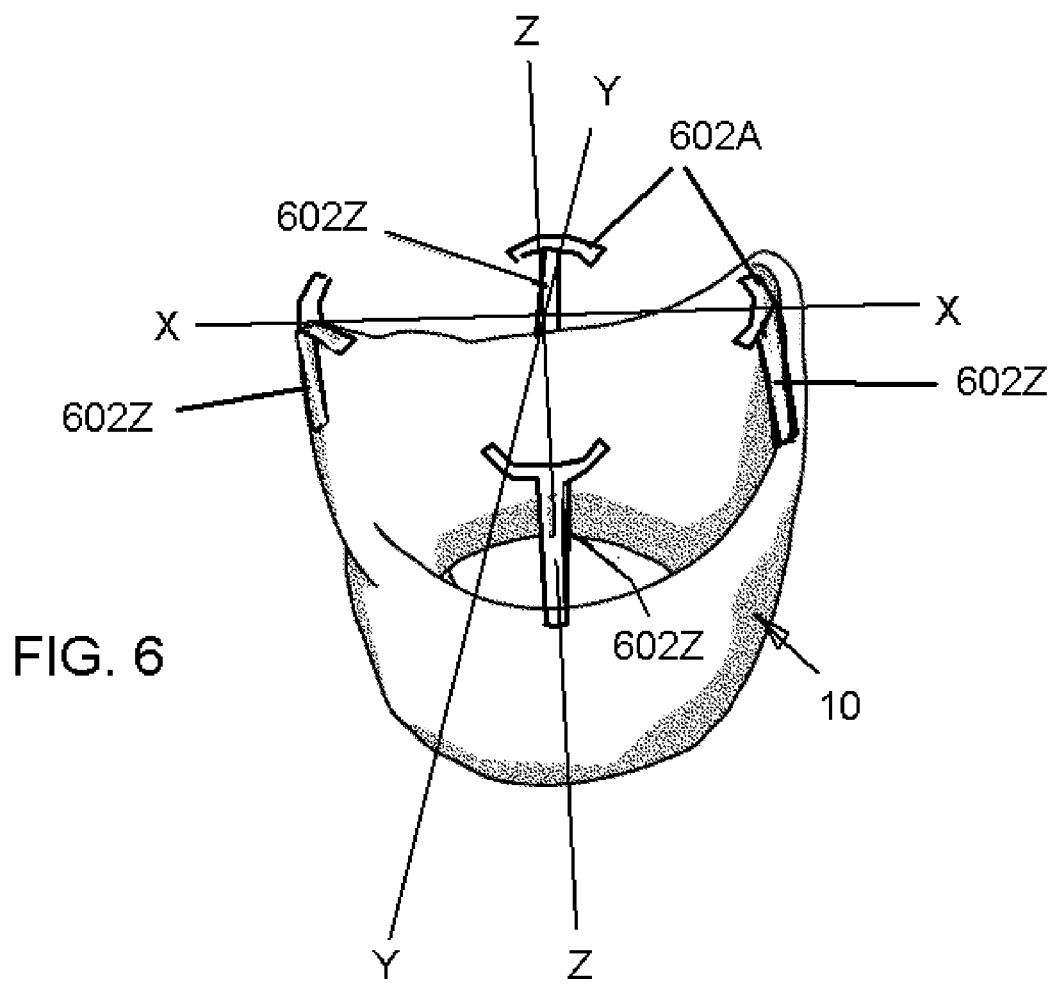
FIG. 6 is a view of a shell like that of FIG. 2, but with orientation directional drilling guide posts extending apically of the shell.
Figure 7:
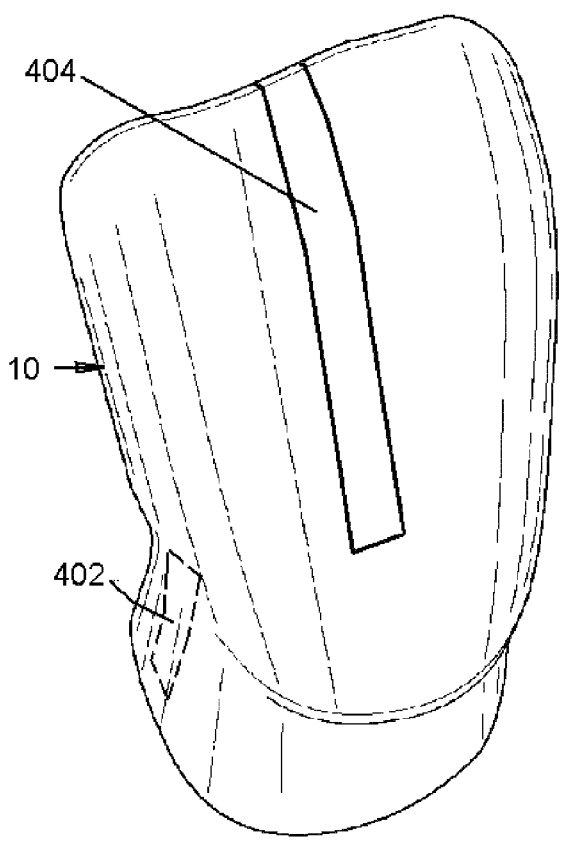
FIG. 7 is a perspective view of another embodiment of the shell with outer markings.

In another embodiment the x, y and z-axis's can be visually provided via the use of winged-posts or post with arc pieces 502A and 60A as depicted in FIGS. 4 and 6. The winged-posts 502A and 602A provide the horizontal intersection of the x-axis and y-axis in the horizontal plane. The intersection of these two points provides a visual point at which the bone drilling bur can be inserted. The vertical arm or post 502X and 602Z of the winged-post provides the z-axis, i.e. vertical axis, to the path of insertion of the bone drilling bur. The wings 502A and 602A at the upper limit of the posts 502 and 602 provide enhanced visual referencing of the vertical winged-posts depicted in FIGS. 4 and 6.

The hollow shell 10 with visual guide markings are positioned within the soft-tissue socket 108 as previously described and shown in FIGS. 3 to 10, 13 and 14. The bone drilling bur 804 and instruments make no physical contact with the hollow shell structure 10, therefore the bone drilling bur is kept independent of the hollow shell guide unlike previous descriptions of bone drilling guides that require the bone drill to make physical contact during use. The hollow shell provides a visual guide and axis orientation without the need of the bone drilling bur to be in direct contact with the surface of the guide.

Yet, another distinction over the prior art is the ability of the hollow shell's ability to stop bleeding during the drilling and implant insertion phase of the procedure. As it is commonly known in the field of dentistry that after a tooth is extracted bleeding occurs from the "fresh" extraction site. The majority of the bleeding is known to come from the exposed soft-tissue. The hollow shell comes into direct contact with the residual socket and exposed soft tissues in which it is difficult to apply direct pressure towards. The hollow shell makes intimate and direct contact to the fresh soft tissue extraction site thus applying physical contact to the exposed bleeding surface of the soft tissue socket, the physical contact of the outer surface to the internal socket of the soft tissue stops the bleeding rapidly. The hollow shell thereby provides improved visualization to the extraction site at a crucial time of bone preparation. The hollow shell via direct contact to the bleeding soft tissue socket allows superior visualization to the extraction site. This greatly aids in the ability of the clinician to drill the bone as it provides a bloodless site during bone drilling. Another distinct advantage of a hollow shell surgical guide is the ability to prevent the soft tissue socket from collapsing after tooth removal. It is known in the field of dentistry that after tooth removal the soft tissue will immediately begin to collapse into the unsupported extraction socket. As the soft tissue collapses into the socket bone drilling preparation is greatly compromised as visualization and obstruction by the soft tissues becomes a complicating factor during the immediate implant placement at the time of tooth extraction. The placement of a hollow shell surgical guide prevents the soft tissue from collapsing and maintains a clear and open visual field for the immediate implant placement. Hence, the surgical guide prevents soft tissue collapse and access to the implant surgical site and it provides the ability to stop bleeding during the drilling and implant insertion phase of treatment, these are additional distinct advantages over the prior art.

It is also anticipated that this hollow shell with visual guide markings and orientation winged-posts and the like (i.e., surgical guide) be also designed and used as a radiographic guide during the diagnostic phase which is present immediately after tooth removal (and prior to immediate implant is placement). This application of the hollow shell with visual guide markings is designed to index the residual soft tissue socket perimeter and the path to be taken in the y-axis, to the underlying bone when viewed on an x-ray or other means of radiographic, digital Scanning, photographic or alternative means of physical recordings or records. In which case the hollow shell could be fabricated from a variety of materials that is radiolucent, such as acrylic, polymers, plastic materials, PEEK material, to allow the x-ray beam to readily pass through such material in combination with orientation markings designed of radio-opaque materials such as gutta-percha, barium liquid, metals paints, etc. as the visual or physical orientation markings upon the surface of the hollow shell. The hollow shell to be placed within the soft-tissue residual socket after a tooth has been removed. A radiograph is then taken prior to drilling of the bone at the time of surgery. The radiographic markings on the surface of the hollow shell would provide directional instruction and insertion orientation to the bone that is below the soft tissue socket. The operator could then reference the bone that is below the soft tissue socket by the visual markings on the hollow shell at the time of surgery. This simplifies the use of bone drilling instruments in the determination of proper directions and insertion. The prior art radiographic guides rely upon position bone and its relative position to adjacent teeth to stabilize a radiographic guide. The hollow shell with orientation markings relies solely on the soft tissue residual socket for stabilization of the guide. The structure of the hollow shells perimeter and ability to replicate the peaks and valleys of the soft tissue establishes an intimate physical fit of the hollow shell to the soft tissue socket. This hollow shell thereby provides a reliable alternative to other radiographic guides described in the prior art. The invention herein described relies solely on the residual soft tissue socket remaining after the extraction of a tooth.

Nowhere in the prior art does a surgical guide or radiographic guide with orientation markings rely solely upon the position of the remaining soft tissue socket as a means to provide instruction or guidance in the direction of drilling and insertion of the immediate dental implant.

The hollow shell with orientation markings provide the relationship between the residual soft-tissue gingival socket relative to the underlying spatial position of the extraction socket and is recorded or noted using a spatial referencing system in the x, y and z, i.e. horizontal, vertical and transverse planes. The preferred embodiment would be in the vertical direction but off axis and a combination of horizontal, vertical and transverse axis is anticipated. The spatial markings provide the relation of the bone to the residual soft-tissue gingival socket and provide important information that is used during bone drilling and implant insertion. After the bone is drilled and the implant is inserted the hollow shell with orientation markings is removed. It is also conceivable that this same hollow shell with orientation markings could be used to fabricate a temporary abutment. The orientation guide hollow shell could be fabricated from a variety of materials but not limited to metals, ceramics, polymers, acrylic, zirconia, composites and other materials typically used.

In more detail and with reference to FIGS. 13 and 14, a soft tissue preserving and drill guide dental implant method of the invention is used immediately after a tooth has been extracted to leave a soft tissue socket 108 having an anatomical shape, and a bone socket 106, the implant hole 810 to be drilled using a drill 802 and bur 804 for receiving an implant 30 (see FIG. 1) at an extraction site. The method includes first providing the hollow dental implant shell 10 having an outer surface conforming substantially to the shape of the soft tissue socket 108 that is left immediately after the tooth extraction from the bone socket, the shell having a plurality of markings 402 and/or 404 and/or 502 and/or 602 that are more opaque to x-rays than the material of the shell so that the markings are clearly visible in an x-ray image of the extraction site.

The dental implant shell 10 is then inserted into the soft tissue socket 108 that was left immediately after tooth extraction from a bone socket. At least one x-ray image of the extraction site is then taken with the shell in the soft tissue socket and the bone socket near the shell. Using the x-ray so the practitioner can see the relationship of the and shell and soft tissue socket to the bone socket, and visual inspection of the actual shell in the soft tissue socket, the drilling of a hole 810 for receiving a dental implant in the area of the bone socket is guided. The dental implant is then inserted into the drilled hole 810 and, according to the invention this is without mechanically connecting the dental implant 30 to the shell 10 so that the shell stays seated in the soft tissue socket without disturbing the shape and anatomy of the soft tissue socket, while the dental implant 30 is seated in the hole 810 at its best orientation.

As noted above, the markings may be inner surface marking 402 on an inner surface of the shell, and/or outer surface markings 404 on the outer surface of the shell, and/or a post 602 extending from the shell, and/or a post 502 extending toward in inner hollow volume of the shell.

Figure 9:
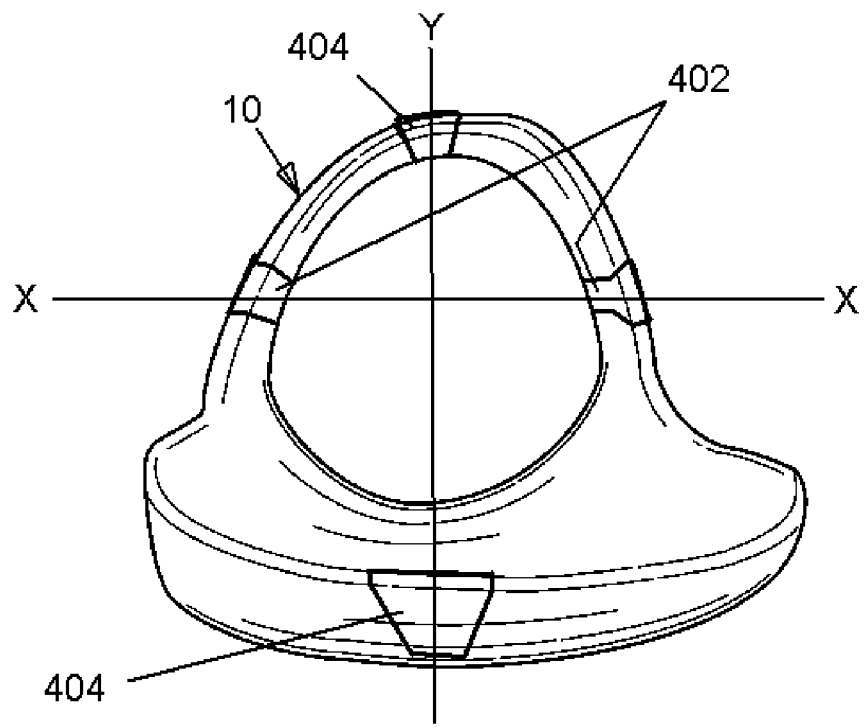
FIG. 9 is top view of the shell of FIGS. 7 and 8, with labial markings.
Figure 10:
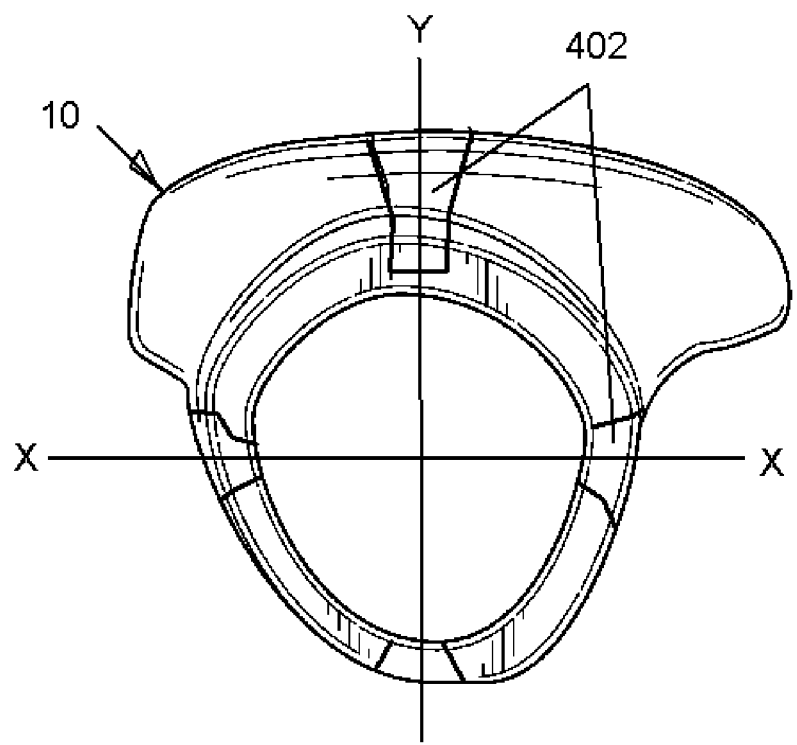
FIG. 10 is bottom view of the shell of FIGS. 7 and 8, with labial markings.

The markings are arranged so that a first pair of markings, for example markings 402, 402 in FIG. 8, are on opposite sides of the shell 10 on an x axis of the shell extending along an arch of a jaw containing the bone socket, a second pair of markings 404, 404 for example in FIG. 9, are on opposite sides of the shell on a y axis of the shell extending lingually and buccally, and at least part of each marking, for example marking posts 602 in FIG. 6, extend on a z axis that is substantially parallel to at least one of a soft tissue axis 12 or the bone socket axis or implant axis 32.

A further and more general object of the invention is to provide a hollow shell with an extended labial (buccal) surface shown in FIGS. 7 to 10. The hollow shell with labial surface would provide an outer shape similar to the curvature of the natural tooth. This hollow shell with veneer would provide a dual purpose of providing additional information and aid in the orientation of the drilling instruments. A second advantage to the hollow shell with labial tooth surface is to provide an easier means in the fabrication of a temporary tooth and abutment for the immediate implant placement after tooth extraction. In the preferred embodiment the hollow shell with labial surface and incisal edge 404 in FIG. 7 could have internal and/or external orientation markings 404. In another embodiment the hollow shell with labial surface and incisal edge would not have internal or external visual markings and would rely upon the physically design solely for orientation and directional information. The hollow shell would be composed of a variety of dental materials including but not limited to metal, acrylic, zirconia, polymers, plastics, peek materials and the like.

The hollow shell with labial tooth surface aids in orientation of bone drilling instruments by providing visual information as to the proper position of the incisal edge of a tooth that is being replaced. The hollow shell with labial tooth surface would insert within the soft tissue extraction socket providing an additional means to the visual orientation of the bone drilling instruments. The labial surface of the hollow shell is extended to the incisal edge thus providing boundaries during bone drilling. It is commonly accepted in the art of implant surgical placement that the long axis of the implant needs to be positioned lingual to the incisal edge of teeth. A hollow shell with a labial surface extending to the incisal edge would provide a structure and means to enable a dental surgeon to direct the bone drilling in the proper orientation described. The hollow shell with labial surface extending to the incisal edge prevents the surgeon from positioning the bur beyond the incisal edge in a buccal direction. This ensures that the immediate dental implants will be orientated in a favorable position by providing a visual aide to the clinician at the time of surgery.

In invention thus sues a hollow shell with orientation markings as a surgical guide and a radiographic guide. The hollow shell with labial surface and incisal edge or these above two devices can be combined (two distinct devices).

While specific embodiments of the invention have been shown and described in detail to illustrate the application of the principles of the invention, it will be understood that the invention may be embodied otherwise without departing from such principles.

What is claimed is:

1. A soft tissue preservation arrangement configured for use in a soft tissue socket immediately after a tooth has been extracted, the arrangement comprising a shell having an outer surface for engaging soft tissue within the soft tissue socket, an inner surface, and a plurality of guide markings spaced around the shell, the inner surface defining a first opening at a top of the shell and a second opening at a bottom of the shell, and the inner surface and the outer surface defining a wall of the shell having a substantially uniform thickness between the top opening and the bottom opening, the plurality of guide markings for aiding a drilling of an implant-receiving bore in a bone socket located below the soft tissue prior to insertion of an implant such that the shell is independent of contact with a bone drilling bur inserted through the first opening and the second opening during the drilling of the implant-receiving bore.

2. The arrangement of claim 1, wherein the markings are radiographic markings made from a material that is more opaque to x-rays than a material of the shell.

3. The arrangement of claim 1, wherein the markings are on the inner surface of the shell.

4. The arrangement of claim 1, wherein the markings are on the outer surface of the shell.

5. The arrangement of claim 1, wherein the markings are each a post extending from the shell.

6. The arrangement of claim 1, wherein the markings are each a post extending toward in an inner hollow volume of the shell.

7. The arrangement of claim 1, wherein the markings each include a post extending in a first direction distally from a surface of the shell and a wing extending from the post in a second direction that is transverse to the first direction.

8. A soft tissue preserving, dental implant arrangement comprising:
a hollow shell including an outer surface and an inner surface extending from a proximal end to a distal end, the outer surface and the inner surface defining a substantially uniform thickness of the shell, the proximal end being defined by a first perimeter that is smaller than a second perimeter defining the distal end such that the shell tapers outwardly from the proximal end to the distal end, the distal end being asymmetrically scalloped with a distal peak, a mesial peak opposite the distal peak, a lingual valley between the distal peak and the mesial peak, and a facial valley opposite the lingual valley, and the first perimeter defining an opening at the proximal end of the hollow shell being larger than a maximum diameter of an implant; and
a plurality of markings that each correspond to a respective one of the distal peak, the mesial peak, the lingual valley, and the facial valley.

9. The arrangement of claim 8, wherein the markings are of a material that is more opaque to x-rays than a material of the shell.

10. The arrangement of claim 8, wherein the markings are on the inner surface of the shell.

11. The arrangement of claim 10, wherein the markings are on the outer surface of the shell.

12. The arrangement of claim 8, wherein the markings are on the outer surface of the shell.

13. The arrangement of claim 8, wherein the markings are each a post extending distally from the shell.

14. The arrangement of claim 8, wherein a first axis in a direction from the marking corresponding to the distal peak to the marking corresponding to the mesial peak and a second axis in a direction from the marking corresponding to the lingual valley to the marking corresponding to the facial valley intersect at an intersection point, the plurality of markings being configured such that the intersection point indicates a target location for drilling into a bone socket when the shell is positioned in a soft tissue socket adjacent to the bone socket.

* * * * *